US012697037B2

(12) United States Patent
Higgins et al.

(10) Patent No.: US 12,697,037 B2
(45) Date of Patent: Aug. 4, 2026

(54) PRENATAL MONITORING SYSTEM

(71) Applicant: Medtronic, Inc., Minneapolis, MN (US)

(72) Inventors: Elise J. Higgins, St. Paul, MN (US); Yong K. Cho, Excelsior, MN (US); Richard J. O'Brien, Hugo, MN (US); Randal C. Schulhauser, Phoenix, AZ (US); Douglas A. Hettrick, White Bear Lake, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 578 days.

(21) Appl. No.: 18/163,173

(22) Filed: Feb. 1, 2023

(65) Prior Publication Data

US 2023/0293023 A1 Sep. 21, 2023

Related U.S. Application Data

(60) Provisional application No. 63/267,557, filed on Feb. 4, 2022.

(51) Int. Cl.
A61B 5/0205 (2006.01)
A61B 5/00 (2006.01)
(Continued)

(52) U.S. Cl.
CPC ...... A61B 5/02055 (2013.01); A61B 5/14532 (2013.01); A61B 5/14551 (2013.01);
(Continued)

(58) Field of Classification Search
CPC ... A61B 5/4343; A61B 5/4362; A61B 5/0022; A61B 5/6823; A61B 2503/02
See application file for complete search history.

(56) References Cited

U.S. PATENT DOCUMENTS

| | | |
|---|---|---|
| 5,404,877 A | 4/1995 | Nolan et al. |
| 6,190,324 B1 | 2/2001 | Kieval et al. |
| | (Continued) | |

FOREIGN PATENT DOCUMENTS

| | | |
|---|---|---|
| EP | 1815784 A1 | 8/2007 |
| WO | 9958056 A1 | 11/1999 |
| | (Continued) | |

OTHER PUBLICATIONS

Allahem et al., "Automated uterine contractions pattern detection framework to monitor pregnant women with a high risk of premature labour", Informatics in Medicine Unlocked, vol. 20, No. 100404, Elsevier, Jan. 29, 2020, 14 pp., URL: https://www.sciencedirect.com/science/article/pii/S2352914820305542?via%3Dihub.

(Continued)

*Primary Examiner* — Tammie K Marlen
(74) *Attorney, Agent, or Firm* — Shumaker & Sieffert, P.A.

(57) ABSTRACT

A system for sensing physiological traits of a maternal patient and a fetal patient carried by the maternal patient during a pregnancy using one or more sensors. The system may use the physiological traits sensed to define a maternal attribute for the maternal patient and a fetal attribute for the fetal patient, such as a heart rate, blood pressure, respiration rate, temperature, oxygen saturation level, or other attributes. The system is configured to compare the maternal attribute to a maternal limit describing a threshold for the maternal patient and/or compare the fetal attribute to a fetal limit describing a threshold for the fetal patient. The system is configured to issue a communication to the maternal patient and/or a clinician based on the comparisons. In examples, the system regularly communicates the maternal (Continued)

attribute and/or the fetal attribute to an output device of the maternal patient and/or a clinician.

14 Claims, 7 Drawing Sheets

(51) Int. Cl.

| | |
|---|---|
| *A61B 5/145* | (2006.01) |
| *A61B 5/1455* | (2006.01) |
| *A61B 5/1464* | (2006.01) |
| *A61B 5/28* | (2021.01) |
| *A61B 5/296* | (2021.01) |
| *A61B 5/344* | (2021.01) |
| *A61B 5/389* | (2021.01) |
| *A61B 5/021* | (2006.01) |
| *A61B 5/024* | (2006.01) |
| *A61B 5/0245* | (2006.01) |
| *A61B 5/08* | (2006.01) |

(52) U.S. Cl.

CPC .............. *A61B 5/1464* (2013.01); *A61B 5/28* (2021.01); *A61B 5/296* (2021.01); *A61B 5/344* (2021.01); *A61B 5/389* (2021.01); *A61B 5/4356* (2013.01); *A61B 5/4362* (2013.01); *A61B 5/7475* (2013.01); *A61B 5/021* (2013.01); *A61B 5/02411* (2013.01); *A61B 5/0245* (2013.01); *A61B 5/0816* (2013.01); *A61B 2503/02* (2013.01); *A61B 2562/04* (2013.01)

(56) References Cited

U.S. PATENT DOCUMENTS

| | | | |
|---|---|---|---|
| 6,312,378 | B1 | 11/2001 | Bardy |
| 6,409,675 | B1 | 6/2002 | Turcott |
| 6,438,407 | B1 | 8/2002 | Ousdigian et al. |
| 6,582,365 | B1 | 6/2003 | Hines et al. |
| 7,188,151 | B2 | 3/2007 | Kumar et al. |
| 7,653,434 | B1 | 1/2010 | Turcott et al. |
| 8,043,213 | B2 | 10/2011 | Hatlestad et al. |
| 9,186,089 | B2 | 11/2015 | Mazar et al. |
| 10,172,593 | B2 | 1/2019 | Shinar et al. |
| 10,278,581 | B2 * | 5/2019 | Gaster .................. A61B 5/6833 |
| 10,413,200 | B2 | 9/2019 | Joseph |
| 10,413,207 | B2 | 9/2019 | Sarkar et al. |
| 10,420,476 | B2 | 9/2019 | Moon et al. |
| 10,610,150 | B2 | 4/2020 | Berry |
| 2004/0100376 | A1 | 5/2004 | Lye et al. |
| 2004/0122487 | A1 | 6/2004 | Hatlestad et al. |
| 2007/0016089 | A1 | 1/2007 | Fischell et al. |
| 2008/0319353 | A1 | 12/2008 | Howell et al. |
| 2010/0268095 | A1 | 10/2010 | Mazar et al. |
| 2013/0053657 | A1 | 2/2013 | Ziarno et al. |
| 2016/0058429 | A1 | 3/2016 | Shinar et al. |
| 2016/0066894 | A1 | 3/2016 | Barton-Sweeney |
| 2016/0174840 | A1 | 6/2016 | Udoh et al. |
| 2016/0374608 | A1 | 12/2016 | Dugan |
| 2017/0224268 | A1 | 8/2017 | Altini et al. |
| 2017/0265807 | A1 | 9/2017 | Stopek |
| 2017/0281001 | A1 | 10/2017 | Stopek |
| 2019/0090742 | A1 | 3/2019 | Hahn et al. |
| 2019/0090743 | A1 | 3/2019 | Hahn et al. |
| 2019/0150776 | A1 | 5/2019 | Bardy et al. |
| 2019/0167139 | A1 | 6/2019 | Bardy |
| 2020/0000441 | A1 | 1/2020 | Lafon et al. |
| 2020/0072782 | A1 | 3/2020 | Hanh et al. |
| 2020/0086110 | A1 | 3/2020 | Karsdon et al. |
| 2020/0113470 | A1 | 4/2020 | Friedman et al. |
| 2020/0196958 | A1 | 6/2020 | Penders et al. |
| 2020/0222032 | A1 | 7/2020 | Stein |
| 2020/0229800 | A1 | 7/2020 | Mena Benito et al. |
| 2021/0113099 | A1 | 4/2021 | Rogers et al. |
| 2021/0162125 | A1 | 6/2021 | Altschul et al. |
| 2021/0257091 | A1 | 8/2021 | Spang et al. |
| 2021/0378585 | A1 | 12/2021 | Daniele et al. |
| 2023/0293024 | A1 | 9/2023 | Higgins et al. |

FOREIGN PATENT DOCUMENTS

| | | |
|---|---|---|
| WO | 2020194350 A1 | 10/2020 |
| WO | 2020243463 A1 | 12/2020 |
| WO | 2021050818 A1 | 3/2021 |

OTHER PUBLICATIONS

Arizton, "Maternity Care Market—Global Outlook and Forecast 2017-2023", Arizton Advisory & Intelligence, 5 pp., Retrieved from the Internet on Apr. 13, 2023 from URL: https://www.arizton.com/market-reports/maternity-care-market#snapshots.

Bezemer et al., "Simultaneous multi-depth assessment of tissue oxygen saturation in thenar and forearm using near-infrared spectroscopy during a simple cardiovascular challenge", Crit Care, vol. 13, No. 5, Nov. 30, 2009, 5 pp., URL: https://ccforum.biomedcentral.com/articles/10.1186/cc8003.

Clifford, "Chapter 15—Blind Source Separation: Principal & Independent Component Analysis", Biomedical Signal and Image Processing, 2008, pp. 1-47, Retrieved from the Internet on Apr. 13, 2023 from URL: http://www.mit.edu/~gari/teaching/6.555/LECTURE_NOTES/ch15_bss.pdf.

Fotiadou et al., "Multi-Channel Fetal ECG Denoising With Deep Convolutional Neural Networks", Frontiers in Pediatrics, vol. 8, No. 508, Aug. 26, 2020, 13 pp., URL: https://www.frontiersin.org/articles/10.3389/fped.2020.00508/full.

Garcia-Canadilla et al., "Machine Learning in Fetal Cardiology: What to Expect", Fetal Diagnosis and Therapy, vol. 47, No. 5, Jan. 7, 2020, pp. 363-372, URL: https://pubmed.ncbi.nlm.nih.gov/31910421/.

GE Healthcare, "Monica Novii Wireless Patch System: Empowering you and your patients", General Electric Company, 2018, 8 pp., Retrieved from the Internet on Apr. 13, 2023 from URL: https://www.womens-health.net/data/files/mic-eu-novii-wireless-patch-system-brochure-english-04-2018-jb25922us3a.pdf.

Hines et al., "Biotelemetry Using Implanted Unit to Monitor Preterm Labor", Tech Briefs Engineering Solutions for Design & Manufacturing, May 1, 1999, 5 pp., URL: https://www.techbriefs.com/component/content/article/tb/pub/briefs/electronics-and-computers/1837.

International Search Report and Written Opinion of International Application No. PCT/IB2023/050914 dated Mar. 24, 2023, 21 pp.

Martin et al., "National Vital Statistics Reports", CDC, vol. 68, No. 13, Nov. 30, 2019, 47 pp., URL: https://www.cdc.gov/nchs/data/nvsr/nvsr68/nvsr68_13-508.pdf.

Medtech Innovator, "Tiny Kicks", 1 pp., Retrieved from the Internet on Apr. 13, 2023 from URL: https://medtechinnovator.org/company/tinykicks/.

Pal et al., "Blind Source Separation: A Review and Analysis", 2013 International Conference Oriental COCOSDA held jointly with 2013 Conference on Asian Spoken Language Research and Evaluation, IEEE, Nov. 25, 2013, 5 pp., URL: https://ieeexplore.ieee.org/abstract/document/6709849.

Raydiant Oximetry, Inc, "Raydiant Oximetry", 5 pp., Retrieved from the Internet on Apr. 13, 2023 from URL: https://www.raydiantoximetry.com/.

The FemTech Focus et al., "The FemTech Focus Podcast with Dr. Brittany Barreto", FemHealth Insights, 12 pp., Retrieved from the Internet on May 1, 2023 from URL: https://www.femtechfocus.com/.

Communication pursuant to Article 94(3) EPC from counterpart European Application No. 23704437.5 dated Mar. 18, 2026, 5 pp.

\* cited by examiner

100

PRENATAL MONITORING SYSTEM

This application claims the benefit of U.S. Provisional Patent Application Ser. No. 63/267,557 (filed Feb. 4, 2022), which is entitled, "PRENATAL MONITORING SYSTEM" and is incorporated by reference herein in its entirety.

TECHNICAL FIELD

This disclosure generally relates to systems including medical devices and, more particularly, to monitoring of prenatal maternal and fetal patients using such systems.

BACKGROUND

Prenatal care checkups are periodically conducted during a pregnancy to evaluate the health and progress of a maternal patient and a fetal patient. During the prenatal care checkup, a clinician may evaluate various physiological traits to assess the continuing health of the maternal patient, such as heartrate to assess cardiac health, blood glucose level to assess any indications of gestational diabetes, blood pressure to assess any indications of preeclampsia, weight gain to assess a high or low weight given the stage of the pregnancy, and other physiological traits of the prenatal maternal patient. The clinician may also evaluate various physiological traits of the fetal patient, such as fetal heartrate and fetal movement. The indications thus obtained are generally tracked over the stages of the pregnancy to assess the health of the maternal patient and the fetal patient as the pregnancy develops. In many cases, the physiological traits of the maternal patient and the fetal patient are assessed using medical equipment located within a medical clinic, such that a physical presence of the maternal patient within the medical clinic is required. This may in turn require frequent in-office visits to the medical clinic due to the understandable concerns of the maternal patient regarding the health of the fetal patient over the course of the pregnancy.

SUMMARY

In general, the disclosure describes a system for sensing physiological traits of a pregnant maternal patient and a fetal patient carried by the pregnant maternal patient during a pregnancy. The system is configured to sense a maternal physiological trait and a fetal physiological trait using one or more sensors implanted subcutaneously and/or positioned cutaneously on the skin, or other sensors accessible to the maternal patient outside of a medical clinic environment. The system may use the physiological traits sensed to define a maternal attribute for the maternal patient and a fetal attribute for the fetal patient, such as a heart rate, blood pressure, respiration rate, temperature, oxygen saturation level, uterine contractions, and/or other attributes. The system is configured to compare the maternal attribute to a maternal limit describing a threshold for the patient and compare the fetal attribute to a fetal limit describing a threshold for the fetal patient. The system is configured to generate an indication for output (e.g., issue a communication or alert) to the maternal patient. In examples, the system regularly or asynchronously communicates the attributes to an output device of the maternal patient, interested participants (e.g., co-parent), and/or a clinician, such that the maternal patient, interested participants (e.g., co-parent), and/or the clinician may remain updated on the various attributes without requiring a physical presence within the medical clinic.

The system may include sensing circuitry operably connected to the one or more sensors. The sensing circuitry may be configured to communicate an output signal indicative of the physical traits sensed to processing circuitry operably connected to the sensing circuitry. The processing circuitry may define the maternal attribute and the fetal attributes using the output signal. The processing circuitry may issue the communication based on a comparison of a maternal attribute with a maternal limit, and/or based on a comparison of a fetal attribute defined using the fetal attribute with a fetal limit.

The system provides for scheduled monitoring (e.g., continuously, hourly, twice per day, or some other schedule without requiring user intervention) using one or more sensors implanted in and/or wearable by the maternal patient. Hence, the system may communicate sensed maternal physiological traits, maternal attributes, fetal physiological traits, and/or fetal attributes more frequently and on a more consistent schedule than might otherwise be available when monitoring requires presence with a medical facility setting and/or a concerted action by the maternal patient or their caregiver/clinician. Further, the sensed patient data and/or prior patient data may be provided to and/or evaluated by a clinician in a more expeditious and consistent manner. In examples, the system is configured to alter its operation based on prior patient data and/or an input received from a clinician IO device. For example, the system may increase or decrease a frequency at which a sensor or group of sensors senses a particular patient physical trait and/or one or more physiological traits sensed by the system, a scheduled basis for providing patient physiological data, one or more maternal limits and/or fetal limits, and/or other operations. Thus, the system may update and/or adjust monitoring of a patient without a necessity for physical visitation to a medical facility and/or with a clinician.

The use of a maternal attribute based on one or more physiological traits sensed from the maternal patient may enhance the detection of conditions of concern for the maternal patient, such as a maximum or minimum heartrate of the maternal patient or fetal patient, a high or low blood pressure of the maternal patient or fetal patient, a high or low oxygen saturation level of the maternal patient or fetal patient, a high or low respiration rate of the maternal patient or fetal patient, a high or low temperature of the maternal patient or fetal patient, or other limits based on a body function of the maternal patient or fetal patient. Typical monitoring of maternal patients and/or fetal patients generally occurs by sensing and evaluating maternal physiological traits and/or fetal physiological traits often individually and/or largely within the setting of a medical facility. Example systems disclosed herein may monitor and define a maternal attribute and/or a fetal attribute using a combination of physiological traits, and further compare the physiological trait to a limit which considers the combined physiological traits.

In examples, the system uses a machine learning algorithm to improve monitoring and/or indications provided to the patient and/or a clinician. The machine learning algorithm may assist in interpreting maternal attributes and/or fetal attributes to, for example, identify whether a condition of concern may be present for the maternal patient and/or fetal patient. For example, processing circuitry of the system may be configured to train the machine learning algorithm using prior patient data and/or prior fetal data sensed for the maternal patient and/or fetal patient, such that a maternal limit and/or fetal limit is based at least in part on physiological traits somewhat specific to the maternal patient and/or fetal patient rather than, for example, based broadly on other metrics which may be relatively insensitive to the specific physiological traits of an individual patient. In examples, the system may incorporate prior patient data obtained by the system to evaluate and/or update maternal limits and/or fetal limits. Hence, the machine learning algorithm may allow the system to provide substantially personalized interpretations, evaluations, and/or communications specific to the individual physiological traits exhibited by the maternal patient and/or fetal patient. Implementing such personalized approaches in the systems and techniques described herein realize an increase in accuracy for detecting true episodes, for instance, by detecting fewer false positives and overlooking fewer false negatives for conditions of concern that may be present in the patient.

The system may improve identification and/or responsiveness to trends and/or indications which might emerge from physiological data collected from a population of users. The system may assist in defining a maternal attribute, a maternal limit, a fetal attribute, a fetal limit, a schedule for sensing physiological traits, and/or other operations based on the population data. For example, the machine learning algorithm may define and/or refine the maternal limit and/or fetal limit using population data sensed from a population of other individual prenatal patients carrying other fetal patients. The machine learning algorithm may be trained using a training data set including the population data. In examples, the system is configured to communicate with a plurality of individual medical devices worn, implanted within, and/or otherwise utilized by the population of other individual prenatal patients. The medical system may communicate with the plurality of individual medical devices to gather the population data. Hence, the machine learning algorithm may allow the system to more rapidly respond to the identification of and use of trends that might emerge as a result of monitoring a broad population of patients.

The techniques and systems of this disclosure may be implemented in a medical device such as an implantable medical device (IMD) that can continuously (e.g., on a periodic or triggered basis without human intervention) sense maternal physiological traits and/or fetal physiological traits while being worn or subcutaneously implanted in a patient over months or years, and perform numerous operations per second on patient data to enable the systems herein to detect potential conditions of concern. Using techniques of this disclosure with an medical device such as an IMD may be advantageous when a physician cannot be continuously present with the patient over weeks or months to evaluate maternal physiological traits and/or fetal physiological traits sensed by the system, and/or where performing the operations of the system on the maternal physiological traits and/or fetal physiological traits (e.g., personalization of maternal and/or fetal limits, incorporation of trends identified from population data) on weeks or months of data gathered through physiological monitoring could not practically be performed in the mind of a physician.

In an example, a system configured to sense physiological attributes of a maternal patient to monitor a pregnancy comprises: one or more sensors configured to sense a maternal physiological trait indicative of a maternal attribute of the maternal patient and a fetal physiological trait indicative of a fetal attribute of a fetal patient carried by the maternal patient, wherein the maternal attribute is indicative of a physiological characteristic of a body of the maternal patient and the fetal attribute is indicative of a physiological characteristic of a body of the fetal patient; sensing circuitry operably coupled to the one or more sensors and configured to issue an output signal indicative of the maternal physiological trait and the fetal physiological trait; and processing circuitry operably connected to the sensing circuitry, wherein the processing circuitry is configured to, receive the output signal from the sensing circuitry, define the maternal attribute and the fetal attribute for each output signal received, issue a communication based on at least one of: a comparison of the maternal attribute and a maternal limit, wherein the maternal limit defines a threshold for the maternal attribute, or a comparison of the fetal attribute and a fetal limit, wherein the fetal limit defines a threshold for the fetal attribute.

In an example, a method comprises: sensing a maternal physiological trait indicative of a maternal attribute of a maternal patient and a fetal physiological trait indicative of a fetal attribute of a fetal patient carried by the maternal patient using one or more sensors, wherein the maternal attribute is indicative of a physiological characteristic of a body of the maternal patient and the fetal attribute is indicative of a physiological characteristic of a body of the fetal patient; receiving, by processing circuitry, an output signal generated by sensing circuitry operably coupled to the one or more sensors, wherein the output signal is indicative of the maternal attribute and the fetal attribute, defining, using the processing circuitry, the maternal attribute and the fetal attribute using the output signal, and issuing a communication, using the processing circuitry, a communication based on at least one of: a comparison of the maternal attribute and a maternal limit, wherein the maternal limit defines a threshold for the maternal attribute, or a comparison of the fetal attribute and a fetal limit, wherein the fetal limit defines a threshold for the fetal attribute.

The details of one or more examples are set forth in the accompanying drawings and the description below. Other features, objects, and advantages will be apparent from the description and drawings, and from the claims.

DETAILED DESCRIPTION

Figure 1:
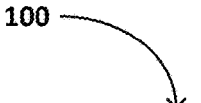
FIG. 1 is a conceptual diagram illustrating an example medical system configured to sense a physiological trait of a maternal patient and a fetal patient carried by the maternal patient.
Figure 1:
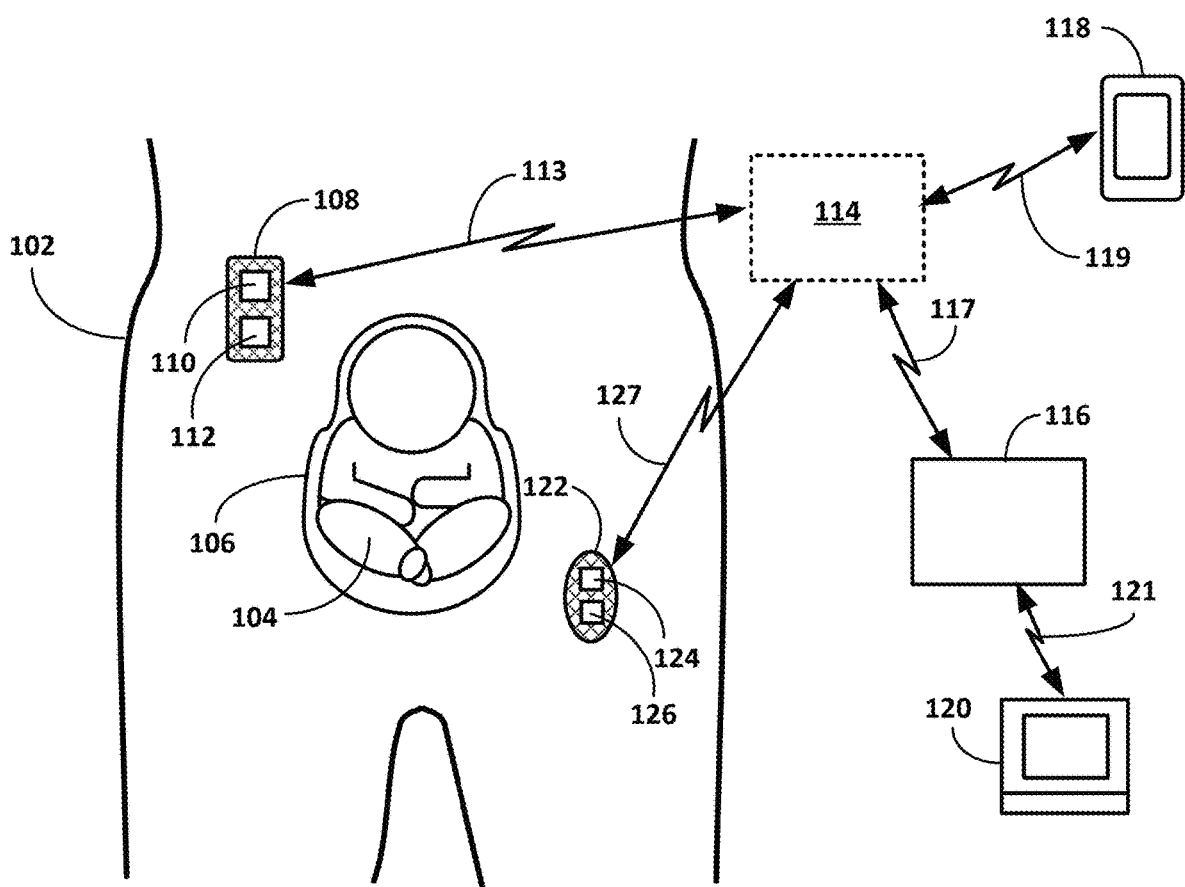

In general, the disclosure describes a system configured to a sense a physiological trait of a maternal patient and a physiological trait of a fetal patient carried by the maternal patient during a pregnancy. The system may use the physiological traits sensed to substantially monitor and track the health of the maternal patient and the fetal patient over the course of the pregnancy when, for example, the maternal patient is outside of a medical clinic setting. The system uses the sensed physiological traits to define a maternal attribute of the maternal patient and a fetal attribute of the fetal patient, such as a heart rate, a blood pressure level (e.g., systolic and/or diastolic), an oxygen saturation level, a respiration rate, a temperature, an activity level, a glucose level, an amniotic fluid level, and/or other attributes of the maternal patient and/or fetal patient. The system is config- ured to provide communications to the maternal patient and/or a clinician indicating, for example, whether the maternal attribute and/or fetal attribute indicate normally expected values, or whether the maternal attribute and/or fetal attribute potentially indicate conditions of concern.

The system is configured to sense the maternal physi- ological trait and the fetal physiological trait using one or more sensors accessible to the maternal patient outside of a medical clinic environment. For example, the one or more sensors may be mechanically supported by a wearable or implantable device. The system may define the maternal attribute and the fetal attribute and communicate informa- tion to the maternal patient and/or a clinician, such that the maternal patient and/or the clinician may remain updated without requiring a physical presence of the maternal patient within the medical clinic. The system may be configured to define and check the maternal attribute and the fetal attribute on a regular schedule (e.g., twice daily), on a schedule based on assessed risk, on a substantially continuous basis, when prompted by the maternal patient, clinician, and/or other user, or some combination thereof. The system may be configured to adjust the schedule based on one or more comparisons of a maternal attribute to a maternal limit and/or one of more comparisons of a fetal attribute to a fetal limit. For example, the system may increase a frequency at which a maternal attribute is monitored based on an increase in occurrences of a maternal attribute exceeding a maternal limit. The system may decrease a frequency at which a maternal attribute is monitored based on an decrease in occurrences of a maternal attribute falling within a maternal limit. The system may increase a frequency at which a fetal attribute is monitored based on an increase in occurrences of a fetal attribute exceeding a fetal limit. The system may decrease a frequency at which a fetal attribute is monitored based on an decrease in occurrences of a fetal attribute falling within a maternal limit.

The system is configured to substantially assess the mater- nal attribute and/or fetal attribute to determine if the mater- nal attribute and/or fetal attribute is a normally expected value (e.g., within a normally expected range) or if the maternal attribute and/or fetal attribute potentially indicates a condition of concern. The system may assess the maternal attribute by comparing the maternal attribute with a maternal limit, where the maternal limit is characteristic of the maternal attribute for a maternal patient in a stage of pregnancy. The system may be configured to assess the fetal attribute by comparing the fetal attribute with a fetal limit, where the fetal limit is characteristic of the fetal attribute for a fetal patient carried by a maternal patient in a stage of pregnancy. The maternal limit and/or fetal limit may describe, for example, a maximum or minimum heartrate of the maternal patient or fetal patient, a high or low blood pressure of the maternal patient or fetal patient, a high or low oxygen saturation level of the maternal patient or fetal patient, a high or low respiration rate of the maternal patient or fetal patient, a high or low temperature of the maternal patient or fetal patient, or other limits based on a body function of the maternal patient or fetal patient. The system is configured to periodically issue a communication indica- tive of the maternal attribute and the fetal attribute to a patient input/output device ("patient IO device") and/or a clinician input/output device ("clinician IO device"), such that the maternal patient and/or the clinician may remain updated.

Unlike some conventional monitoring and detection sys- tems, the techniques and systems of this disclosure may use a machine learning algorithm to more accurately determine whether one or more sensed maternal attributes and/or fetal attributes indicate a condition of concern for the maternal patient or the fetal patient. In some examples, the machine learning algorithm is trained with a set of training data comprised of and/or indicative of previously received patient physiological data, fetal physiological data, and/or an assessment input of a clinician. Because the machine learn- ing algorithm is trained with potentially thousands or mil- lions of training instances (e.g., training input vectors), the machine learning algorithm may offer improved perfor- mance in the detection of conditions of concern during a pregnancy when compared to conventional pregnancy moni- toring systems and/or techniques. For example, the system may more expeditiously and/or accurately detect indications of preeclampsia, gestational diabetes, unexpected heart rates, unexpected blood pressures, false labors, changes in amniotic fluid, and/or other prenatal conditions potentially placing the maternal patient and/or fetal patient at risk.

Additionally, the techniques and systems of this disclo- sure may be implemented in a medical device such an IMD and/or wearable device that can continuously and/or peri- odically sense maternal physiological traits and/or fetal physiological traits without human intervention and perform millions of operations per second on physiological data to identify conditions of concern with the machine learning algorithm. Using techniques of this disclosure with a medi- cal device such as an IMD and/or wearable device may be advantageous when a physician cannot be continuously present with the patient over weeks or months to gather and evaluate physiological data and/or where performing mil- lions of operations on weeks or months of physiological data could not practically be performed in the mind of a physician using the techniques of this disclosure (e.g., techniques employing a machine learning algorithm).

The maternal physiological trait and/or fetal physiological trait sensed by the system may be any physiological trait sensible by the one or more sensors and influenced by a body function of the maternal patient and/or the fetal patient. For example, maternal physiological trait and/or fetal physi- ological trait may include an electrocardiogram ("ECG"), echocardiogram, electromyography, impedance magnitude, optical signal, a pressure magnitude, an accelerometry read- ing, an audible sound, and/or any other physiological trait influenced by a body function of the maternal patient and/or the fetal patient. The maternal attribute and/or fetal attribute may be any measure of anatomical function that may be inferred from the one or more physiological traits, such as a heart rate of the maternal patient and/or fetal patient, a blood pressure of the maternal patient and/or fetal patient, an oxygen saturation level (e.g., an SpO2 and/or StO2) of the maternal patient and/or fetal patient, a respiration rate of the maternal patient and/or fetal patient, a body temperature of the maternal patient and/or fetal patient, an activity level of the maternal patient and/or fetal patient, or some other anatomical function of the maternal patient and/or fetal patient. The system is configured to compare the define the maternal attribute and the fetal attribute using the one or physiological traits sensed.

The maternal attribute may be based substantially on an individual maternal attribute, a plurality of maternal attributes defined over a time frame, a trend of maternal attributes, and/or some other characteristic of one or more maternal attributes indicative of a state of the maternal patient. The maternal attribute may be based on a combination of substantially different physiological traits indicative of substantially different physiological measures, such as heart rate and blood pressure, respiration rate and muscular contractions, and/or other combinations indicative of substantially different physiological measures. In similar manner, the fetal attribute defined using the fetal attribute may be based substantially on an individual fetal attribute, a plurality of fetal attributes defined over a time frame, a trend of fetal attributes, an/or some other characteristic of one or more fetal attributes indicative of a state of the fetal patient. The fetal attribute may be based on a combination of substantially different fetal physical parameters indicative of substantially different physiological measures, such as heart rate and blood pressure, respiration rate and fetal activity level, and/or other combinations indicative of substantially different physiological measures. The maternal attribute and/or fetal attribute may be based on any singular attribute or combination of attributes indicating a physiological state of the maternal patient and/or the fetal patient.

The system may issue the communication indicative of the maternal attribute and/or fetal attribute defined to a patient input/output (IO) device (e.g., a phone, a tablet, or another IO device) to provide an indication to the maternal patient of the maternal attribute and/or fetal attribute defined. The system may issue the communication indicative of the maternal attribute and/or fetal attribute to an external device (e.g., a server storing a medical database), such that the external device may provide an indication of the maternal attribute and/or fetal attribute to a clinician using a clinician IO device (e.g., a workstation or other clinician IO device) communicatively coupled to the external device. In some examples, the system is configured to provide recommendations to the maternal patient to take an action in response to the communication. For example, the system might recommend the maternal patient contact a clinician and/or medical facility, go to labor and delivery triage at the hospital, stand and/or walk, and/or make other recommendations. In some examples, the system is configured such that the clinician may input the recommendations to the maternal patient using the clinician IO device, and the system may communicate the recommendations from the clinician IO device to the patient IO device.

In examples, the system is configured to adjust the maternal limit, the fetal limit, the patient physiologic trait sensed, the fetal physiologic trait sensed, the maternal attribute, and/or the fetal attribute defined based on a stage of the pregnancy. The system may be configured to receive a designated start of a pregnancy from, for example, the clinician IO device and/or the patient IO device. The system may be configured to determine an elapsed time (e.g., a number of weeks, a certain number of trimesters, etc.) since the designated start of the pregnancy and adjust the maternal limit, the fetal limit, the patient physiologic trait sensed, the fetal physiologic trait sensed, the maternal attribute, and/or the fetal attribute based on the elapsed time. For example, the system may begin sensing a fetal physiological trait indicative of a fetal heartrate and/or fetal activity based on the elapsed time. The system may adjust a maternal limit and/or fetal limit such as a weight gain threshold, a fetal activity threshold, or another maternal limit and/or fetal limit based on the elapsed time. In some examples, the system may adjust a schedule by which the system senses a maternal physiological trait and/or a fetal physiological trait based on the elapsed time.

In addition to issuing the communication based on the maternal attribute, maternal limit, fetal attribute, and fetal limit, the system may be configured to record and/or store the periodically sensed maternal physiological traits, maternal attributes, fetal physiological traits, and/or fetal attributes to enable a clinician and/or the maternal patient to review a history over some portion of or substantially the entirety of a pregnancy. The system may be configured to record and/or store the periodically sensed maternal physiological traits, maternal attributes, fetal physiological traits, and/or fetal attributes to provide the history. In examples, the system is configured to communicate the sensed maternal physiological traits, maternal attributes, fetal physiological traits, and/or fetal attributes on a scheduled basis (e.g., twice daily), such that the history remains substantially updated. The system may communicate the sensed maternal physiological traits, maternal attributes, fetal physiological traits, and/or fetal attributes to the external device to indicate the history to a clinician using the clinician IO device. The system may communicate the sensed maternal physiological traits, maternal attributes, fetal physiological traits, and/or fetal attributes to the patient IO device to indicate the history to the prenatal patient or another user. In some examples, the system is configured to communicate a first set of the sensed maternal physiological traits, maternal attributes, fetal physiological traits, and/or fetal attributes sensed physiological traits and/or attributes to the external device for review by a clinician and communicate a second set of the sensed maternal physiological traits, maternal attributes, fetal physiological traits, and/or fetal attributes to the patient IO device for review by the prenatal patient or other user. The first set communicated to the clinician IO device may be different from or substantially similar to the second set communicated to the patient IO device.

The system includes one or more sensors configured to sense the maternal physiological trait and/or fetal physiological trait. The system may include sensing circuitry operably connected to the one or more sensors. The sensing circuitry may be configured to communicate an output signal indicative of the maternal physiological trait and/or fetal physiological trait sensed to processing circuitry operably connected to the sensing circuitry. The processing circuitry may be configured to cause the one or more sensors and/or the sensing circuitry to communicate (e.g., periodically communicate) the output signal. The processing circuitry may be configured to receive (e.g., periodically receive) the output signal and define the maternal attribute and/or fetal attribute using the output signal. In examples, the system includes a medical device mechanically supporting one or more of the sensors. The medical device may be, for example, an implantable medical device ("IMD") or other medical device configured to remain with and/or accessible to the maternal patient when the maternal patient is in an ambulatory state (e.g., outside of a clinic setting). The medical device may mechanically support at least some portion of the sensing circuitry and/or the processing circuitry. In some examples, the medical device mechanically supports a first portion of the processing circuitry and/or sensing circuitry, and an external device separate from (e.g., displaced from) the medical device mechanically supports a second portion of the processing circuitry. The medical device may include communications circuitry configured to cause the first portion of the processing circuitry to communicate with the second portion of the processing circuitry to, for example, issue a communication indicative of an assessment of a maternal attribute and/or fetal attribute, record and/or store the periodically sensed maternal physiological traits, maternal attributes, fetal physiological traits, and/or fetal attributes, or for other reasons.

In examples, the system is configured to sense a plurality of maternal physiological traits and/or a plurality of fetal physiological traits using the one of more sensors. The system may be configured to define a plurality of maternal attributes using the plurality of maternal physiological traits and/or a define a plurality of fetal attributes using the plurality of fetal physiological traits. The maternal limit and/or fetal limit may be dependent on one or more of the plurality of maternal attributes and/or plurality of fetal attributes defined. For example, a maternal limit may be dependent on a single maternal attribute (e.g., blood glucose level indicative of, for example, gestational diabetes), and the system may issue the communication based on comparison of the single maternal attribute defined and the singly-dependent maternal limit. The maternal limit may be dependent on a combination of maternal attributes defined (e.g., patient heartrate and uterine muscular contractions indicative of, for example, false labor), and the system may issue the communication based on a comparison of the combination of multiple maternal attributes defined and the multiply-dependent maternal limit. Likewise, the system may issue the communication based on comparison of a single fetal attribute defined and a singly-dependent fetal limit dependent on the single fetal attribute, and/or may issue the communication based on comparison of a combination of fetal attributes defined with a multiply-dependent fetal limit dependent on the combination of fetal attributes.

The system (e.g., the processing circuitry) may be configured to define and/or refine the maternal limit and/or fetal limit to reduce a rate of false positives when comparing the maternal attribute to the maternal limit and/or the fetal attribute to the fetal limit. For example, the system may be configured to utilize the periodically sensed maternal physiological traits, patient parameters indicative of the maternal physiological traits, and/or maternal attributes (also termed "patient physiological data") to define and/or refine the maternal limit. The system may be configured to utilize the periodically sensed fetal physiological traits, fetal parameters indicative of the fetal physiological traits, and/or fetal attributes (also termed "fetal physiological data") to define and/or refine the fetal limit. In examples, the system (e.g., the processing circuitry) implements a machine learning algorithm trained with a training data set based on the patient physiological data and/or the fetal physiological data. The machine learning algorithm may be configured to define and/or refine the maternal limit using the patient physiological data and/or define and/or refine the fetal limit using the fetal physiological data.

In examples, the system is configured to receive an assessment input from a user input device (e.g., the patient IO device and/or the clinician IO device) indicative of an assessment of whether the system issued an appropriate communication (e.g., an appropriately tiered communication) when a set of patient physiological data and/or a set of fetal physiological data was previously received. The training data set of the machine learning algorithm may be based on the previously received patient physiological data, fetal physiological data, and/or the assessment input, such that the communications may be substantially tailored to the physiological traits of the individual maternal patient and/or the individual fetal patient. The substantial tailoring to the individual maternal patient and/or individual fetal patient may reduce a rate of false positives indicating necessary action communicated by the system.

In some examples, the system (e.g., the processing circuitry) may be configured to define and/or refine the maternal limit and/or fetal limit based on population data sensed from a population of other individual prenatal patients carrying other fetal patients. The system (e.g., the processing circuitry) may include a machine learning algorithm configured to define and/or refine the maternal limit and/or fetal limit using the population data. In examples, the machine learning algorithm is trained using a training data set including the population data. The population data may include, for example, individual maternal physiological traits sensed from the individual prenatal patients, individual patient parameters based on the individual maternal physiological traits, individual maternal attributes defined for the individual prenatal patients, individual fetal physiological traits sensed from the other fetal patients, individual fetal parameters based on the individual fetal physiological traits, and or individual fetal attributes defined for the other fetal patients. In examples, an external device of the system may be configured to communicate with a plurality of individual medical devices worn, implanted within, and/or otherwise utilized by the population of other individual prenatal patients. The medical system may communicate with the plurality of individual medical devices to gather the population data.

In examples, the medical system may be implemented using one or more computer programs implemented on programmable computers, such as computers that include, for example, processing capabilities, data storage (e.g., volatile or nonvolatile memory and/or storage elements), input devices, and output devices. Program code and/or logic described herein may be applied to input data to perform the functionality described herein and generate desired output information. The programs may be stored on any suitable device, e.g., a storage media, readable by a general or special purpose program running on a computer system (e.g., including processing apparatus) and configuring the computer system to perform functions described herein. Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g., a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a conceptual diagram illustrating an example medical system 100 configured to sense maternal physiological traits of a maternal patient 102 and fetal physiological traits of a fetal patient 104 to monitor a pregnancy. Maternal patient 102 carries fetal patient 104 within a uterus 106 of maternal patient 102. System 100 includes one or more medical devices such as medical device 108. Medical device 108 may mechanically support and/or otherwise be operably coupled to sensor 110 and sensing circuitry 112. System 100 includes processing circuitry 114. In examples, system 100 includes an external device 116. Processing circuitry 114 may be mechanically supported by medical device 108 or external device 116. In examples, medical device 108 mechanically supports a first portion of processing circuitry 114 and external device 116 mechanically supports a second portion of processing circuitry 114. System 100 may include patient IO device 118 and/or clinician IO device 120.

Sensor 110 is configured to sense a maternal physiological trait of maternal patient 102 and/or a fetal physiological trait of fetal patient 104. The maternal physiological trait and/or fetal physiological trait may be some measurable phenomena generated by the body of maternal patient 102 and/or the body of fetal patient 104 indicative of a maternal attribute of maternal patient 102 and/or a fetal attribute of fetal patient 104. For example, the maternal physiological trait and/or fetal physiological trait may be an electrocardiogram ("ECG"), echocardiogram, electromyography, impedance magnitude, optical signal, a pressure magnitude, an accelerometry reading, an audible sound, and/or any other physiological trait influenced by a body of maternal patient 102 and/or a body of fetal patient 104. In some examples, the ECG is a maternal ECG ("mECG"). In some examples the ECG is a fetal ECG ("fECG"). The maternal attribute and/or fetal attribute may be any measure of anatomical function that may be inferred from the maternal physiological trait and/or fetal physiological trait, such as a heart rate of maternal patient 102 and/or fetal patient 104, a blood pressure of maternal patient 102 and/or fetal patient 104, an oxygen saturation level of maternal patient 102 and/or fetal patient 104, a respiration rate of maternal patient 102 and/or fetal patient 104, a body temperature of maternal patient 102 and/or fetal patient 104, an activity level of maternal patient 102 and/or fetal patient 104, or some other anatomical function of maternal patient 102 and/or fetal patient 104.

In examples, medical device 108 is configured to position relative to maternal patient 102 such that sensor 110 may sense the maternal physiological trait and/or a fetal physiological trait. Medical device 108 may be, for example, an implantable device configured to implant within maternal patient 102 to position sensor 110. Medical device 108 may be a device configured to substantially non-invasively contact a body of maternal patient 102 to position sensor 110 (e.g., smartwatch and/or other smart apparel). Medical device 108 may be a device configured to position sensor 110 through a manipulation by and/or action of maternal patient 102 (e.g., a weight scale, a blood pressure cuff, urine sampling device, and/or a glucose testing device). Although described primarily in the context of examples in which medical device 108 takes the form of a device configured to be implanted within maternal patient 102, the techniques of this disclosure may be implemented in systems including any one or more implantable or external devices configured to position sensor 110 such that sensor 110 may to sense a physiological trait of maternal patient 102 and/or fetal patient 104. In some examples, medical device 108 may be an insertable cardiac monitor or loop recorder, such as that disclosed in U.S. patent application Ser. No. 15/081,216, incorporated herein by reference in its entirety.

Sensing circuitry 112 is configured to communicate (e.g., via link 113) an output signal to processing circuitry 114 indicative of the maternal physiological trait and/or the fetal physiological trait sensed by sensor 110. Processing circuitry 114 is configured to define the maternal attribute of maternal patient 102 and/or the fetal attribute of fetal patient 104 using the output signal. For example, processing circuitry 114 may be configured to define a maternal attribute such as a heartrate, a systolic blood pressure, a diastolic blood pressure, an oxygen saturation (e.g., an SpO2 indicative of blood oxygen saturation and/or an StO2 indicative of tissue oxygen saturation), a respiration rate, a body temperature, a blood glucose level, a body weight, a muscle contraction, an activity level, an amniotic fluid level, and/or other maternal attribute of maternal patient 102 using the output signal. Processing circuitry 114 may be configured to define a fetal attribute such as a heartrate, a systolic blood pressure, a diastolic blood pressure, an oxygen saturation, a respiration rate, a body temperature, a blood glucose level, a body weight, a muscle contraction, an activity level, and/or other fetal attribute of fetal patient 104 using the output signal. Processing circuitry 114 is configured to issue a communication to patient IO device 118, external device 116, and/or clinician IO device 120 indicative of the maternal attribute and/or fetal attribute, such that patient 102 and/or the clinician may remain updated during the course of a pregnancy.

In examples, processing circuitry 114 is configured to communicate at least some portion of the patient physiological data sensed and/or defined (e.g., the maternal physiological trait, a patient parameter indicative of the maternal physiological trait, and/or the maternal attribute) to patient IO device 118, external device 116, and/or clinician IO device 120. Processing circuitry 114 may be configured to communicate at least some portion of the fetal physiological data sensed or defined (e.g., the fetal physiological trait, a fetal parameter indicative of the fetal physiological trait, and/or the fetal attribute) to patient IO device 118, external device 116, and/or clinician IO device 120. In some examples, processing circuitry 114 is configured to communicate a first portion of the patient physiological data and/or fetal physiologic data to patient IO device 118 and a second portion of the patient physiological data and/or fetal physiological data to external device 116 such that, for example, patient IO device 118 displays information useful to maternal patient 102 while external device 116 causes the display of additional and/or different information which might be useful to a clinician.

In examples, patient IO device 118, external device 116, and/or clinician IO device 120 may take the form of personal computing devices of maternal patient 102 and/or a clinician, such as a smartphone, smartwatch, or other smart apparel of maternal patient 102 or the clinician. Patient IO device 118, external device 116, and/or clinician IO device 120 may be any computing device configured for wireless communication with processing circuitry 114, such as a desktop, laptop, or tablet computer, a smart home controller, alarm, thermostat, speaker, or other smart appliance, or any Internet of Things (IoT) device. Patient IO device 118, external device 116, and/or clinician IO device 120 may be configured to communicate with processing circuitry 114 and each other according to the Bluetooth® or Bluetooth® Low Energy (BLE and/or BTLE) protocols, as examples.

Processing circuitry 114 is configured to compare the maternal attribute to a maternal limit and/or compare the fetal attribute to a fetal limit to substantially monitor maternal patient 102 and/or fetal patient 104. The maternal limit and/or fetal limit may define, for example, a maximum or minimum heartrate, a maximum or minimum systolic blood pressure, a maximum or minimum diastolic blood pressure, a maximum or minimum oxygen saturation level, a maximum or minimum respiration rate, a maximum or minimum body temperature, a maximum or minimum body weight, a maximum or minimum blood glucose level, a maximum or minimum activity level, a maximum or minimum amniotic fluid level, and/or some other defined maternal limit and/or fetal limit. Processing circuitry 114 may be configured to issue the communication to patient IO device 118 (e.g., via link 119), external device 116 (e.g., via link 117), and/or clinician IO device 120 (e.g., via link 121 or another communication link) based on the comparison. Processing circuitry 114 may be configured to cause patient IO device 118, external device 116, and/or clinician IO device 120 to provide an output sensible (e.g., able to be sensed) by the prenatal patient, a clinician, or another user when processing circuitry 114 issues the communication. For example, the sensible output may include a visual output, audio output, haptic output, or some other output which may be sensed by one or more of the senses of a human being.

In examples, processing circuitry 114 may be configured to issue the communication using a tiered communication indicative of an assessment of the comparison. The tiered communication system may provide for earlier and/or more accurate notifications to the maternal patient and/or a clinician that a pregnancy may be assessed as a high risk pregnancy which may introduce potential complications for the maternal patient and/or fetal patient. For example, the tiered communication system may provide an indication that preeclampsia, gestational diabetes, and/or other prenatal conditions potentially placing the maternal patient and/or fetal patient at risk may have occurred or could potentially occur.

Processing circuitry 114 may be configured to define a tier of a communication based on a plurality of individual maternal limits (e.g., a first maternal limit, a second maternal limit, and/or a third maternal limit) and/or a plurality of individual fetal limits (e.g., a first fetal limit, a second fetal limit, and/or a third fetal limit). For example, processing circuitry 114 may be configured to issue a Tier I communication when the maternal attribute and/or fetal attribute are assessed to be a normally expected value (e.g., within a range defined by the first maternal limit and/or the first fetal limit). Processing circuitry 114 may be configured to issue a Tier II communication when the maternal attribute and/or fetal attribute are assessed to potentially indicate a condition warranting further evaluation and/or action by patient 102 and/or a clinician (e.g., within a range defined by the second maternal limit and/or the second fetal limit.) Processing circuitry 114 may be configured to issue a Tier III communication when the maternal attribute and/or fetal attribute are assessed to indicate a condition potentially more serious and/or warranting more urgent action and/or action by patient 102 and/or a clinician (e.g., within a range defined by the third maternal limit and/or the third fetal limit.). The tiered communication system may define any number of tiers and any number of maternal limits and/or fetal limits. In some examples, processing circuitry 114 may be configured to cause patient IO device 118 and/or clinician IO device 120 to provide visible, audible, or other indicia associated with a tier of the communication. For example, processing circuitry 114 may be configured to cause patient IO device 118 and/or clinician IO device 120 to provide a first indicia (e.g., a green background) for a Tier I communication, a second indicia (e.g., a yellow background) for a Tier II communication, and/or a third indicia (e.g., a red background) for a Tier III communication.

Processing circuitry 114 may be configured to assign a different tier to a communication indicative of the maternal attribute and a communication indicative of the fetal attribute. For example, processing circuitry 114 may be configured to issue a Tier I patient communication when the maternal attribute is assessed as a normally expected value, a Tier II patient communication when the maternal attribute is assessed to potentially indicate a condition warranting further evaluation and/or action by patient 102 and/or clinician, and Tier III patient communication when the maternal attribute is assessed to indicate a condition potentially more serious and/or warranting more urgent action and/or action by the patient and/or clinician. Processing circuitry 114 may be configured to issue a Tier I fetal communication when the fetal attribute is assessed as a normally expected value, a Tier II fetal communication when the fetal attribute is assessed to potentially indicate a condition warranting further evaluation and/or action by the patient and/or clinician, and Tier III fetal communication when the fetal attribute is assessed to indicate a condition potentially more serious and/or warranting more urgent action and/or action by the patient and/or clinician. Processing circuitry 114 may assign the tier to the patient communication substantially independently of a tier assigned to the fetal communication, and vice-versa.

In addition to or instead of issuing the communications, processing circuitry 114 may be configured to record and/or store the patient physiological data and/or fetal physiological data periodically sensed to enable a clinician and/or maternal patient 102 to review a history over some portion of or substantially the entirety of a pregnancy and postpartum. For example, processing circuitry 114 may be configured to communicate the patient physiological data and/or fetal physiological data from medical device 108 to external device 116, clinician IO device 120, and/or patient IO device 118. Processing circuitry 114 may be configured to communicate the patient physiological data and/or fetal physiological data on a scheduled basis (e.g., twice daily, or on some other schedule), such that the history remains substantially updated. In examples, processing circuitry 114 is configured to alter the operation of medical system 100 based on an input received from clinician IO device 120, based on one or more tiered communications, and/or for other reasons. For example, processing circuitry 114 may cause medical system 100 to increase or decrease a frequency at which sensor 110 senses a particular patient physical trait and/or fetal physiological trait based on a received input from clinician IO device 120, based on one or more tiered communications, and/or for other reasons. Processing circuitry 114 may cause medical system 100 to alter and/or adjust one or more maternal physiological traits and/or fetal physiological traits sensed by medical device 108 based on a received input from clinician IO device 120, based on one or more tiered communications, and/or for other reasons. Processing circuitry 114 may cause medical system 100 to alter and/or adjust the scheduled basis by which processing circuitry 114 provides the patient physiological data and/or fetal physiological data to external device 116 based on a received input from clinician IO device 120, based on one or more tiered communications, and/or for other reasons. Processing circuitry 114 may cause medical system 100 to alter and/or adjust one or more maternal limits and/or fetal limits used by processing circuitry 114 based on a received input from clinician IO device 120, based on one or more tiered communications, and/or for other reasons.

In some examples, medical system 100 includes a plurality of sensors. The plurality of sensors may be configured to sense a maternal physiological trait and/or fetal physiological trait of maternal patient 102 and/or fetal patient 104. For example, medical system 100 may include a second medical device 122 including a sensor 124 and/or sensing circuitry 126. Sensing circuitry 126 may be configured to communicate (e.g., via link 127) an output signal to processing circuitry 114 indicative of a maternal physiological trait and/or fetal physiological trait sensed by sensor 124. For example, medical device 108 may be configured to primarily sense a maternal physiological trait and define a maternal attribute. Medical device 122 may be configured to primarily sense a fetal physiological trait and define a fetal attribute. In other examples, processing circuitry may be configured to define a maternal attribute and/or fetal attribute using maternal physiological traits and/or fetal physiological traits sensed from both medical device 108 and medical device 122. Second medical device 122 may mechanically support at least some portion of processing circuitry 114. Second medical device 122, sensor 124, and/or sensing circuitry 126 may be configured similar to medical device 108, sensor 124, and/or sensing circuitry 112 respectively. In some examples, second medical device 122 is configured to contact the body of maternal patient 102 at a location different from the location of medical device 108 to, for example, more effectively sense the fetal physical characteristic, and/or for some other reason. In some examples, medical device 122 may be an insertable cardiac monitor or loop recorder, such as that disclosed in U.S. patent application Ser. No. 15/081,216, incorporated herein by reference in its entirety.

In some examples, medical system 100 (e.g., an electrode of sensor 110, 124) is configured to sense a signal indicative of an ECG of maternal patient 102 (e.g., an mECG), a signal indicative of an ECG of fetal patient 104 (e.g., an fECG), and/or a mixed ECG signal indicative of both the ECG of maternal patient 102 and the ECG of fetal patient 104. Processing circuitry 114 may be configured to define a maternal attribute indicative of a heartrate of maternal patient 102 and a fetal attribute indicative of a heartrate of fetal patient 104 using the output signal provided by sensing circuitry 112, 126. Processing circuitry 114 may compare the maternal attribute to a maternal limit indicative of a maximum heart rate of maternal patient 102 or a minimum heart rate of maternal patient 102. Processing circuitry 114 may compare the fetal attribute to a fetal limit indicative of a maximum heart rate of fetal patient 104 or a minimum heart rate of fetal patient 104. Processing circuitry 114 may issue a communication to patient IO device 118, external device 116, and/or clinician IO device 120 based on the comparison of the maternal attribute and the maternal limit and/or the comparison of the fetal attribute and the fetal limit.

For example, processing circuitry 114 may compare the heartrate of maternal patient 102 to a maximum heartrate (e.g., 100 beats/minute (bpm)) and/or a minimum heartrate (e.g., 60 bpm). Processing circuitry 114 may compare the heartrate of fetal patient 104 to a maximum heartrate (e.g., 160 bpm) and/or a minimum heartrate (e.g., 110 bpm). Processing circuitry 114 may issue a tiered communication based on the maximum heartrate, the minimum heartrate, and/or determined deviations therefrom.

In some examples, medical system 100 (e.g., an optical sensor of sensor 110, 124) is configured to sense a signal indicative of a blood pressure of maternal patient 102, a signal indicative of a blood pressure of fetal patient 104, and/or a mixed blood pressure signal indicative of both the blood pressure of maternal patient 102 and the blood pressure of fetal patient 104. Processing circuitry 114 may be configured to define a maternal attribute indicative of a systolic pressure and/or diastolic pressure of maternal patient 102 and a fetal attribute indicative of a systolic and/or diastolic pressure of fetal patient 104 using the output signal provided by sensing circuitry 112, 126. Processing circuitry 114 may compare the maternal attribute to a maternal limit indicative of a maximum systolic pressure of maternal patient 102, minimum systolic pressure of maternal patient 102, maximum diastolic pressure of maternal patient 102, or a minimum diastolic pressure of maternal patient 102. Processing circuitry 114 may compare the fetal attribute to a fetal limit indicative of a maximum systolic pressure of fetal patient 104, minimum systolic pressure of fetal patient 104, maximum diastolic pressure of fetal patient 104, or a minimum diastolic pressure of fetal patient 104. Processing circuitry 114 may issue a communication to patient IO device 118, external device 116, and/or clinician IO device 120 based on the comparison of the maternal attribute and the maternal limit and/or the comparison of the fetal attribute and the fetal limit.

For example, processing circuitry 114 may compare the systolic pressure of maternal patient 102 to a maximum systolic pressure (e.g., 130 mmHg) and/or a minimum systolic pressure (e.g., 100 mmHg). Processing circuitry 114 may compare the systolic pressure of fetal patient 104 to a maximum systolic pressure (e.g., 75 mmHg) and/or a minimum systolic pressure (e.g., 65 mmHg). Processing circuitry 114 may compare the diastolic pressure of maternal patient 102 to a maximum diastolic pressure (e.g., 80 mmHg) and/or a minimum diastolic pressure (e.g., 60 mmHg). Processing circuitry 114 may compare the systolic pressure of fetal patient 104 to a maximum systolic pressure (e.g., 50 mmHg) and/or a minimum systolic pressure (e.g., 40 mmHg). Processing circuitry 114 may issue a tiered communication based on the maximum systolic pressure, minimum systolic pressure, maximum diastolic pressure, minimum diastolic pressure, and/or determined deviations therefrom.

In some examples, medical system 100 (e.g., an optical sensor of sensor 110, 124) is configured to sense a signal indicative of an oxygen saturation of maternal patient 102, a signal indicative of an oxygen saturation of fetal patient 104, and/or a mixed oxygen saturation signal indicative of both the oxygen saturation of maternal patient 102 and the oxygen saturation of fetal patient 104. Processing circuitry 114 may be configured to define a maternal attribute indicative of an oxygen saturation level of maternal patient 102 and a fetal attribute indicative of an oxygen saturation level of fetal patient 104 using the output signal provided by sensing circuitry 112, 126. Processing circuitry 114 may compare the maternal attribute to a maternal limit indicative of a maximum oxygen saturation level of maternal patient 102 or a minimum oxygen saturation level of maternal patient 102. Processing circuitry 114 may compare the fetal attribute to a fetal limit indicative of a maximum oxygen saturation level of fetal patient 104 or a minimum oxygen saturation level of fetal patient 104. Processing circuitry 114 may issue a communication to patient IO device 118, external device 116, and/or clinician IO device 120 based on the comparison of the maternal attribute and the maternal limit and/or the comparison of the fetal attribute and the fetal limit.

For example, processing circuitry 114 may compare the oxygen saturation of maternal patient 102 to a maximum oxygen saturation (e.g., 100%) and/or a minimum oxygen saturation (e.g., 95%). Processing circuitry 114 may compare the oxygen saturation of fetal patient 104 to a maximum oxygen saturation (e.g., 52%) and/or a minimum oxygen saturation (e.g., 46%). Processing circuitry 114 may issue a tiered communication based on the maximum oxygen saturation, the minimum oxygen saturation, and/or determined deviations therefrom.

In some examples, medical system 100 (e.g., an accelerometer and/or an electrode of sensor 110, 124) is configured to sense a signal indicative of a respiration of maternal patient 102, a signal indicative of a respiration of fetal patient 104, and/or a mixed respiration signal indicative of both the respiration of maternal patient 102 and the respiration of fetal patient 104. Processing circuitry 114 may be configured to define a maternal attribute indicative of a respiration rate of maternal patient 102 and a fetal attribute indicative of a respiration rate of fetal patient 104 using the output signal provided by sensing circuitry 112, 126. Processing circuitry 114 may compare the maternal attribute to a maternal limit indicative of a maximum respiration rate of maternal patient 102 or a minimum respiration rate of maternal patient 102. Processing circuitry 114 may compare the fetal attribute to a fetal limit indicative of a maximum respiration rate of fetal patient 104 or a minimum respiration rate of fetal patient 104. Processing circuitry 114 may issue a communication to patient IO device 118, external device 116, and/or clinician IO device 120 based on the comparison of the maternal attribute and the maternal limit and/or the comparison of the fetal attribute and the fetal limit.

For example, processing circuitry 114 may compare the respiration rate of maternal patient 102 to a maximum respiration rate (e.g., 16 breaths per minute (bpm)) and/or a minimum respiration rate (e.g., 12 bpm). Processing circuitry 114 may compare the respiration rate of fetal patient 104 to a maximum respiration rate (e.g., 70 bpm) and/or a minimum respiration rate (e.g., 30 bpm). Processing circuitry 114 may issue a tiered communication based on the maximum respiration rate, the minimum respiration rate, and/or determined deviations therefrom.

In some examples, medical system 100 (e.g., an resistive network and/or an optical sensor of sensor 110, 124) is configured to sense a signal indicative of a temperature of maternal patient 102, a signal indicative of a temperature of fetal patient 104, and/or a mixed temperature signal indicative of both the temperature of maternal patient 102 and the temperature of fetal patient 104. Processing circuitry 114 may be configured to define a maternal attribute indicative of a body temperature of maternal patient 102 and a fetal attribute indicative of a body temperature of fetal patient 104 using the output signal provided by sensing circuitry 112, 126. Processing circuitry 114 may compare the maternal attribute to a maternal limit indicative of a maximum temperature of maternal patient 102 or a minimum temperature of maternal patient 102. Processing circuitry 114 may compare the fetal attribute to a fetal limit indicative of a maximum temperature of fetal patient 104 or a minimum temperature of fetal patient 104. Processing circuitry 114 may issue a communication to patient IO device 118, external device 116, and/or clinician IO device 120 based on the comparison of the maternal attribute and the maternal limit and/or the comparison of the fetal attribute and the fetal limit.

For example, processing circuitry 114 may compare the temperature of maternal patient 102 to a maximum temperature (e.g., 99.3 degrees F.) and/or a minimum temperature (e.g., 97.9 degrees F.). Processing circuitry 114 may compare the temperature of fetal patient 104 (e.g., a temperature of maternal patient 102+1 degree f) to a maximum temperature and/or a minimum temperature. Processing circuitry 114 may issue a tiered communication based on the maximum temperature, the minimum temperature, and/or determined deviations therefrom.

In some examples, medical system 100 (e.g., an electrode of sensor 110, 124) is configured to sense a signal indicative of an electromyography signal of maternal patient 102, a signal indicative of an electrohysterography signal of maternal patient 102, or another signal indicative of a muscle contraction (e.g., a uterine muscle contraction) of maternal patient 102. Processing circuitry 114 may be configured to define a maternal attribute indicative of the muscle contraction of maternal patient 102 using the output signal provided by sensing circuitry 112, 126. In examples, the maternal attribute is indicative of a repetition of the sensed muscle contraction (e.g., a pattern of muscle contractions versus time). Processing circuitry 114 may compare the maternal attribute to a maternal limit indicative of a maternal labor experienced by maternal patient 102 or a false labor experienced by maternal patient 102. Processing circuitry 114 may issue a communication to patient IO device 118, external device 116, and/or clinician IO device 120 based on the comparison of the maternal attribute and the maternal limit.

In some examples, medical system 100 (e.g., an glucose sensor of sensor 110, 124, and/or an electrode (e.g., an electrooxidizing anode) of sensor 110, 124) is configured to sense a a glucose signal of maternal patient 102, a signal indicative of a glucose level of maternal patient 102 (e.g., an mECG), or another signal indicative of a glucose level of maternal patient 102 (e.g., an optical signal). Processing circuitry 114 may be configured to define a maternal attribute indicative of the glucose level of maternal patient 102 using the output signal provided by sensing circuitry 112, 126. Processing circuitry 114 may compare the maternal attribute to a maternal limit indicative of a maximum glucose level of maternal patient 102 (potentially indicating gestational diabetes) or a minimum glucose level of maternal patient 102. Processing circuitry 114 may issue a communication to patient IO device 118, external device 116, and/or clinician IO device 120 based on the comparison of the maternal attribute and the maternal limit.

In some examples, medical system 100 (e.g., an electrode of sensor 110, 124) is configured to sense an impedance or another signal indicative of an amniotic fluid level of maternal patient 102. Processing circuitry 114 may be configured to define a maternal attribute indicative of the amniotic fluid level maternal patient 102 using the output signal provided by sensing circuitry 112, 126. In examples, the maternal attribute is indicative of a volume and/or a change in volume of amniotic fluid expected for maternal patient 102. Processing circuitry 114 may issue a communication to patient IO device 118, external device 116, and/or clinician IO device 120 based on the comparison of the maternal attribute and the maternal limit.

Figure 2:
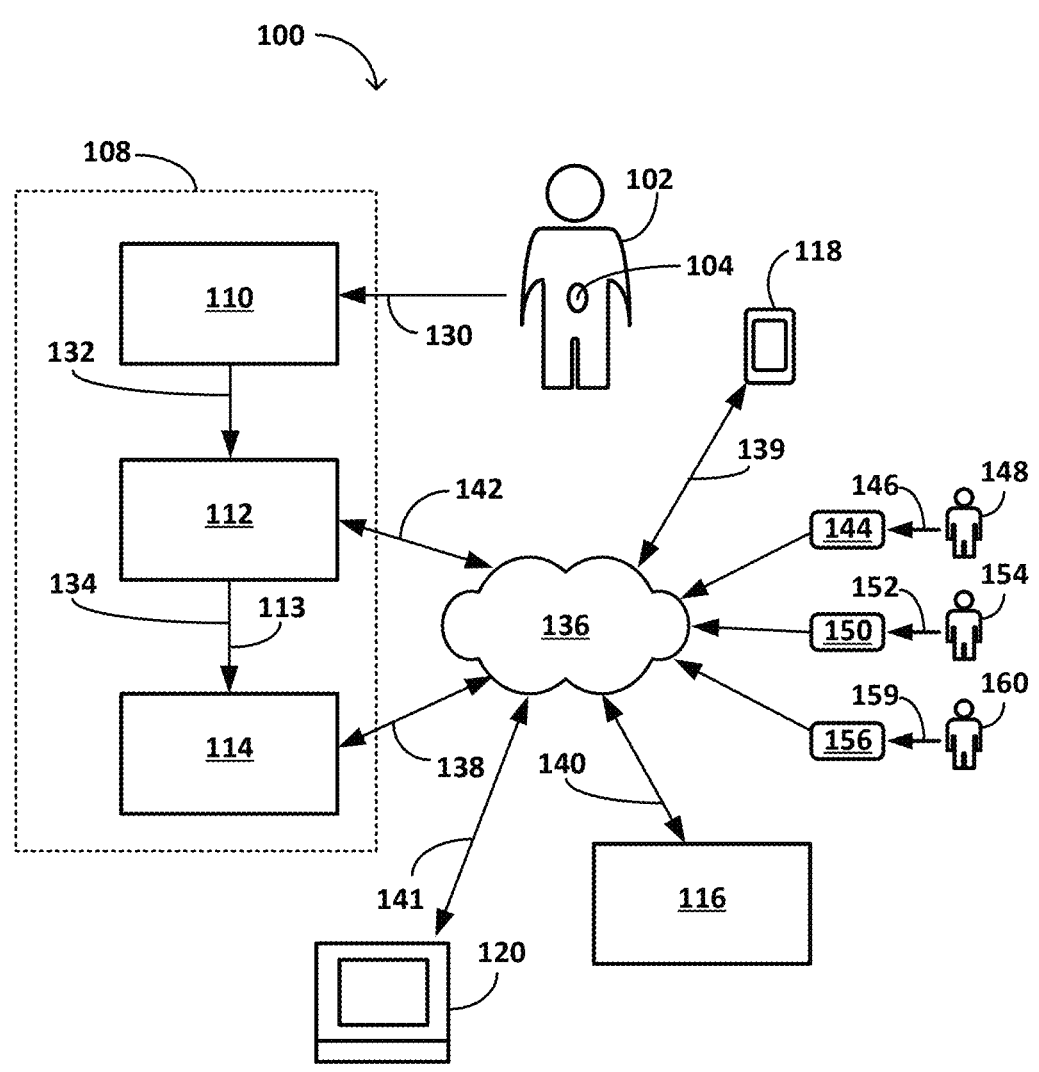
FIG. 2 is a block diagram illustrating example communications of the medical system of FIG. 1.

FIG. 2 illustrates a block diagram of an example technique conducted by medical system 100 to monitor a maternal physiological trait of maternal patient 102 and/or a fetal physiological trait of fetal patient 104. Sensor 110 may sense input information 130 generated by the body of maternal patient 102 and/or the body of fetal patient 104 and provide output information 132 to sensing circuitry 112. The input information may be indicative of a maternal physiological trait and/or fetal physiological trait, such as a cardiac activity, systolic and/or diastolic blood pressure, oxygen saturation, respiration rate, a body temperature, muscular activity, emitted light, audible sound, a weight, a glucose level, or other physiological trait from which a maternal attribute and/or fetal attribute may be inferred. Sensing circuitry 112 may be configured to convert the output information 132 into an output signal 134 usable by processing circuitry 114, such as a digital electrical signal, an analog electrical signal, an optical signal, and/or or some other signal. Processing circuitry 114 is configured to receive output signal 134 (e.g., via link 113 (FIG. 1)) and define a maternal attribute of maternal patient 102 and/or a fetal attribute of fetal patient 104 using output signal 134. Processing circuitry is configured to issue a communication to patient IO device 118, external device 116, and/or clinician IO device 120 based on a comparison of the maternal attribute with a maternal limit and/or a comparison of the fetal attribute with a fetal limit.

Processing circuitry 114 may be configured to communicate with patient IO device 118, external device 116, and/or clinician IO device 120 via a network 136. For example, similar to the use of link 119 (FIG. 1), processing circuitry 114 may be configured to communicate with patient IO device 118 via network 136 using link 138 and link 139. Similar to the use of link 117 (FIG. 1), processing circuitry 114 may be configured to communicate with external device 116 via network 136 using link 138 and link 140. Processing circuitry 114 may be configured to communicate with clinician IO device 120 via network 136 using link 138 and link 141. In examples, similar to the use of link 121 (FIG. 1), external device 116 is configured to communicate with clinician IO device 120 via network 136 using link 140 and link 141. In some examples, sensing circuitry 112 is configured to communicate with processing circuitry 114 (e.g., to communicate the output signal 134) via network 136 using link 142 and link 138.

Processing circuitry 114 may transmit data (e.g., patient physiological data and/or fetal physiological data) received from sensing circuitry 112 to patient IO device 118, external device 116, and/or clinician IO device 120 via network 136. Clinician IO device 120, external device 116, and or patient IO device 118 may comprise computing devices configured to allow users, e.g., clinicians treating maternal patient 102 and other patients, to interact with data collected from sensing circuitry 112. In some examples, sensor 110, sensing circuitry 112, processing circuitry 114, clinician IO device 120, external device 116, and/or patient IO device 118 include one or more handheld computing devices, computer workstations, servers, or other networked computing devices. In some examples, sensor 110, sensing circuitry 112, and/or at least some portion of processing circuitry 114 is mechanically supported by medical device 108.

Network 136 may include one or more computing devices (not shown), such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 136 may include one or more networks administered by service providers, and may thus form part of a large-scale public network infrastructure, e.g., the Internet. Network 136 may provide circuitry and/or devices, such as processing circuitry 114, sensing circuitry 112, external device 116, clinician IO device 120, and/or patient IO device 118, access to the Internet, and may provide a communication framework that allows processing circuitry 114, sensing circuitry 112, external device 116, clinician IO device 120, and/or patient IO device 118 to communicate with one another. In some examples, network 136 may include a private network that provides a communication framework that allows processing circuitry 114, sensing circuitry 112, external device 116, clinician IO device 120, and/or patient IO device 118 to communicate with each other, but isolates one or more of these devices or data flows between these device from devices external to the private network for security purposes. In some examples, the communications between processing circuitry 114, sensing circuitry 112, external device 116, clinician IO device 120, and/or patient IO device 118 are encrypted.

Medical device 108 may mechanically support at least some portion of processing circuitry 114. In some examples, medical device 108 mechanically supports a first portion of processing circuitry 114, and external device 116, clinician IO device 120, patient IO device 118, and/or network 136 mechanically supports a second portion of processing circuitry 114. Processing circuitry 114 may include any circuitry and/or devices of external device 116, clinician IO device 120, patient IO device 118, and/or network 136 to perform the techniques described herein. In examples, processing circuitry 114 is configured to utilize population data sensed from a population of other individual prenatal patients carrying other fetal patients. In examples, external device 116 and/or network 136 is configured to communicate with a plurality of individual medical devices worn, implanted within, and/or otherwise utilized by the population of other individual prenatal patients to gather the population data. For example, external device 116 and/or network 136 may be configured to communicate with individual medical device 144 (e.g., via link 146) to sense physiological traits from a patient 148, communicate with individual medical device 150 (e.g., via link 152) to sense physiological traits from a patient 154, and/or communicate with individual medical device 156 (e.g., via link 159) to sense physiological traits from a patient 160.

Sensor 110 may include any devices, circuitry, structures, reagents, or other materials configured such that sensor 110 may sense input information 130 indicative of a maternal physiological trait of maternal patient 102 and/or a fetal physiological trait of fetal patient 104. For example, sensor 110 may include an electrode configured to sense an electric potential, an impedance, a current, and/or some other electrical phenomena influenced by a body function of maternal patient 102 and/or fetal patient 104 (e.g., to sense an ECG signal, an electromyography signal, a temperature, a glucose level, and/or some other physiological trait). Sensor 110 may include a sound transducer configured to sense a sound wave influenced by (e.g., generated by and or reflected by) a body of maternal patient 102 and/or fetal patient 104 (e.g., to sense an echocardiogram signal, a generated sound, and/or some other physiological trait). Sensor 110 may include a light transmitter and/or receiver configured to transmit light to and/or sense light emitted from (e.g., reflected by) a body of maternal patient 102 and/or fetal patient 104 (e.g., to sense a blood pressure, an oxygen saturation, and/or some other physiological trait). Sensor 110 may include an accelerometer configured to sense a motion generated by a body of maternal patient 102 and/or fetal patient 104 (e.g., to sense a patient activity level, a fetal activity level, a respiration, and/or some other physiological trait). Sensor 110 may include a force transducer configured to sense a force imparted from a body of maternal patient 102 and/or fetal patient 104 (e.g., to sense a patient weight, a blood pressure, and/or some other physiological trait).

Sensing circuitry 112 is configured to receive the output information 132 from sensor 110 and issue output signal 134 to processing circuitry 114. In some examples, sensor 110 includes a first sensor configured to sense a maternal physiological trait of maternal patient 102 and a second sensor configured to sense a fetal physiological trait of fetal patient 104, and output signal 134 includes a first output signal indicative of the maternal physiological trait and a second output signal indicative of the fetal physiological trait. In some examples, sensor 110 is configured to sense a mixed physiological trait indicative of both a maternal physiological trait and a fetal physiological trait, and output signal 134 is a mixed output signal indicative of both the maternal physiological trait and the fetal physiological trait.

Processing circuitry 114 may be configured to define any maternal attribute indicative of a physiological characteristic of maternal patient 102 and/or any fetal attribute indicative of a physiological characteristic of fetal patient 104 using output signal 134. In examples, processing circuitry 114 is configured to define a maternal attribute including one or more of a heart rate of maternal patient 102, a systolic pressure of maternal patient 102, a diastolic pressure of maternal patient 102, an oxygen saturation level of maternal patient 102, a respiration rate of maternal patient 102, and a temperature of maternal patient 102. Processing circuitry 114 may be configured to define a fetal attribute including one or more of a heart rate of fetal patient 104, a systolic pressure of fetal patient 104, a diastolic pressure of fetal patient 104, an oxygen saturation level of fetal patient 104, a respiration rate of fetal patient 104, and a temperature of fetal patient 104. Processing circuitry 114 is configured to compare the maternal attribute to a maternal limit and/or compare the fetal attribute to a fetal limit to substantially monitor maternal patient 102 and/or fetal patient 104. The maternal limit and/or fetal limit may define any threshold for a maternal attribute and/or fetal attribute, including a maximum or minimum heartrate, a maximum or minimum systolic blood pressure, a maximum or minimum diastolic blood pressure, a maximum or minimum oxygen saturation level, a maximum or minimum respiration rate, a maximum or minimum body temperature, a maximum or minimum body weight, a maximum or minimum blood glucose level, a maximum or minimum activity level, or some other defined maternal limit and/or fetal limit.

In examples, processing circuitry 114 is configured to receive a mixed output signal indicative of both the maternal physiological trait and a fetal physiological trait and define the maternal attribute and the fetal attribute using the mixed output signal. Processing circuitry 114 and/or sensing circuitry 112 may be configured to preprocess the mixed output signal (e.g., using linear filtering or another preprocessing technique) to enhance a patient signal source indicative of the maternal attribute and/or a fetal signal source indicative of the fetal attribute. In examples, processing circuitry 114 is configured to use a machine learning algorithm to, for example, improve an accuracy of and/or reduce input requirements of the patient signal source and/or the fetal signal source. In examples, processing circuitry 114 is configured to use at least a first mixed output signal and a second mixed output signal to define the maternal attribute and the fetal attribute. The first mixed output signal and the second mixed output signal may be indicative of the patient signal source and the fetal signal source. For example, the first mixed output signal may be indicative of a mixed physiological trait sensed using a first sensing element (e.g., a first electrode) of sensor 110 or sensor 124 (FIG. 1). The second mixed output signal may be indicative of a mixed physiological trait sensed using a second sensing element (e.g., a second electrode) of sensor 110 or sensor 124 (FIG. 1). In examples, a first medical device (e.g., medical device 108) provides the first mixed output signal and a second medical device (e.g., medical device 122) provides the second mixed output signal.

In some examples, processing circuitry 114 is configured to perform some portion of or substantially all of the signal separation technique to define the maternal attribute and the fetal attribute. In some examples, processing circuitry 114 is configured to communicate data indicative of the mixed output signal to an circuitry of another device (e.g., external device 116, network 136, patient IO device 118, and/or clinician device 120) and receive a communication indicative of the maternal attribute and/or fetal attribute from the other device. Processing circuitry 114 may be configured to define the maternal attribute and/or the fetal attribute using the communication indicative of the maternal attribute and/or fetal attribute received from the other device.

Processing circuitry 114 may be configured to define and/or refine the maternal limit and/or fetal limit to, for example, reduce a rate of false positives when comparing the maternal attribute to the maternal limit and/or the fetal attribute to the fetal limit. In examples, processing circuitry 114 is configured to utilize a machine learning algorithm trained with a training data set based on the patient physiological data and/or the fetal physiological data sensed using sensor 110 to define and/or refine the maternal limit and/or fetal limit. In examples, processing circuitry 114 is configured to receive an assessment input from a user input device (e.g., clinician IO device 120) indicative of an assessment of whether processing circuitry 114 issued an appropriate communication (e.g., an appropriately tiered communication) when a previously received set of patient physiological data ("prior patient data") and/or a previously received set of fetal physiological data ("prior fetal data") was communicated. Processing circuitry 114 may be configured to train the machine learning algorithm using the prior patient data, prior fetal data, and/or the assessment input provided, such that the maternal limit and/or fetal limit may be substantially personalized to maternal patient 102 and/or fetal patient 104. In examples, rather than or in addition to being provided from a user input device, the assessment input may be accessed by processing circuitry 114 via one or more of medical device 108, second medical device 122, external device 116, patient input/output device 118, network 136, or another portion of system 100.

In examples, processing circuitry 114 is configured to formulate one or more training data sets using the assessment input (e.g., from clinician IO device 120) and at least one of the prior patient data or the prior fetal data. A training data set formulated may include a plurality of training input vectors representative of the prior patient data and/or the prior fetal data and a plurality of training output vectors representative of the assessment input received for the prior patient data and/or fetal input data, with each training input vector associated with a corresponding training output vector. Processing circuitry 114 may formulate a given input vector by defining one or more elements of the given input vector, where the one or more elements are indicative of some portion of the prior patient data and/or some portion of the prior fetal data. Processing circuitry 114 may formulate an associated training output vector by defining one or more elements of the associated training output vector, where the one or more elements of the training output vector are indicative of the assessment input received. The assessment input received may indicate, for example, whether a training input vector described or is likely to describe one or more conditions of concern for the maternal patient and/or fetal patient.

Processing circuitry 114 may group each training input vector and associated training output vector in a data pair, such that processing circuitry 114 formulates a plurality of data pairs. Processing circuitry 114 may define a training data set using the plurality of data pairs and, in some examples, train the machine learning algorithm using the training data set. Once trained with the training data set, the machine learning algorithm may be trained to receive a current input vector indicative of patient physiological data and/or fetal physiological data and map the current input vector onto an output space defined at least in part by the plurality of training output vectors. Processing circuitry 114 may define and/or refine the maternal limit and/or fetal limit based on the output space defined. In examples, processing circuitry 114 is configured to compare the maternal attribute to the maternal limit and/or compare the fetal attribute to the fetal limit based on the mapping of the current input vector onto the output space defined. In some examples, the maternal limit and/or the fetal limit defines a vector within the output space.

In examples, processing circuitry 114 may be configured to define and/or refine the maternal limit and/or fetal limit using a machine learning algorithm trained using population data sensed from a population of other individual prenatal patients carrying other fetal patients (e.g., patient 148, patient 154, and/or patient 160). The machine learning algorithm may be trained using the population data. For example, machine learning algorithm may be trained using a population training data set including a plurality of population input vectors representative of the population data and a plurality of population output vectors indicative of an associated evaluation input. A population input vector may describe, for example, physiological data received for an individual prenatal patient and/or other fetal patient within the population. An evaluation input may indicate, for example, whether a population input vector described one or more conditions of concern for the individual prenatal patient and/or other fetal patient. Each population input vector may be associated with a population output vector. Once trained with the population training data set, the machine learning algorithm may be trained to receive a current input vector indicative of patient physiological data and/or fetal physiological data and map the current input vector onto a population output space defined at least in part by the plurality of population output vectors. Processing circuitry 114 may define and/or refine the maternal limit and/or fetal limit based on the population output space defined. In examples, processing circuitry 114 is configured to compare the maternal attribute to the maternal limit and/or compare the fetal attribute to the fetal limit based on the mapping of the current input vector onto the population output space defined. In some examples, the maternal limit and/or the fetal limit defines a vector within the population output space.

In examples, processing circuitry 114 is configured to gather the population data from the population of other individual prenatal patients carrying other fetal patients (e.g., patient 148, patient 154, and/or patient 160). For example, processing circuitry 114 may be configured to communicate with individual medical device 144 to collect physiological traits from individual prenatal patient 148, communicate with individual medical device 150 to collect physiological traits from individual prenatal patient 154, and/or communicate with individual medical device 156 to collect physiological traits from individual prenatal patient 160. Processing circuitry 114 may be configured to formulate the population training data set using the population data gathered. In examples, processing circuitry is configured to train the machine learning algorithm using the population training data set.

Processing circuitry 114 may include one or more processing circuits configured to implement the machine learning algorithm, such as a neural network, a deep learning system, or another type of machine learning system. In examples, processing circuitry 114 is configured to implement the machine learning algorithm using one or more neural network systems, deep learning systems, or other types of supervised or unsupervised machine learning systems. For example, the machine learning algorithm may be implemented by a feedforward neural network, such as a convolutional neural network, a radial basis function neural network, a recurrent neural network, a modular or associative neural network. Examples of machine learning algorithms that may be so configured to perform aspects of this disclosure can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LSTM), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In examples, a neural network utilized by processing circuitry 114 includes a plurality of artificial neurons. The artificial neurons may be present within one or more layers of the neural network. For example, the artificial neurons may present within an input layer of the neural network, an output layer of the neural network, and one or more hidden layers between the input layer and the output layer. The input layer may include one or more input artificial neurons. The output layer may include one or more output artificial neurons. The artificial neurons may be configured to receive a signal at an input of the artificial neuron and process the signal at an output of the artificial neuron (e.g., process the signal using a parameter of the artificial neuron). The artificial neuron may include a plurality of inputs and a plurality of outputs. The artificial neuron may be configured to receive the input from the output of a separate artificial neuron, and may be configured to pass the processed signal from its output to the input of another artificial neuron. The processing of the signal conducted by the artificial neuron may be adjusted by the artificial neuron as training of the machine learning algorithm proceeds. Processing circuitry 114 may be configured to train the machine learning algorithm using the training data set and/or population training data set in any manner causing the machine learning algorithm to converge as the training proceeds. In examples, processing circuitry 114 is configured to use a first portion of the training data set and/or population training data set to cause the machine learning algorithm to converge and a second portion of the training data set and/or population training data set to validation test and/or blind test the training conducted with the first portion.

As discussed, any of external device 116, clinician IO device 120. Patient IO device 118, network 136, and/or medical devices 108, 122, 144, 150, 156 may include, mechanically support, and/or house some portion of or substantially all of processing circuitry 114. Any of external device 116, clinician IO device 120. Patient IO device 118, network 136, and/or medical devices 108, 122, 144, 150, 156 may perform any of the functionality ascribed to processing circuitry 114. Likewise, any of any of external device 116, clinician IO device 120. Patient IO device 118, network 136, and/or medical devices 108, 122, 144, 150, 156 may perform any of the functionality ascribed to any other of external device 116, clinician IO device 120. Patient IO device 118, network 136, and/or medical devices 108, 122, 144, 150, 156. In some examples, some or substantially all of the functionality ascribed to processing circuitry 114 may be performed by one or more devices and/or circuitries not shown in FIG. 2.

System 100 (e.g., processing circuitry 114) may also be configured to retrieve data regarding maternal patient 102 and/or fetal patient 104 from electronic health records (EHR) via, for example, network 136. The EHR may include data regarding historical (e.g., baseline) physiological parameter values, previous health events and treatments, disease states, comorbidities, demographics, height, weight, and body mass index (BMI), as examples, of patients including maternal patient 102 and/or fetal patient 104. System 100 may use data from the EHR to configure algorithms implemented by processing circuitry 114, medical device 108, and/or other devices within system 100 to detect and/or define maternal attributes, fetal attributes, maternal limits, and or fetal limits.

Detection of maternal attributes, fetal attributes, maternal limits, and or fetal limits can be achieved by looking at a number of possible maternal physiological traits and/or fetal physiological traits that occur prior to and while defining a maternal attribute, fetal attribute, maternal limit, and or fetal limit. The advantageous markers to detect an impending or ongoing event may be determined based on an etiology of the patient. The etiology of maternal patient 102 and/or fetal patient 104 may include baseline characteristics, medical history, or disease state. The etiology may include any EHR data, as well as patient activity level or metabolite level. With such possible inputs, processing circuitry 114 may be configured to determine maternal physiological traits and/or fetal physiological traits to exhibit certain trends or threshold crossings to detect an impending or ongoing acute health event, e.g., one or more of a maternal attribute, fetal attribute, maternal limit, and or fetal limit. In some examples, system 100 may be configured to utilize a set of rules to determine one or more maternal attributes, fetal attributes, maternal limits, and or fetal limits. System 100 may be configured to modify the rule set to modify certain rules (e.g., turn certain rules on or off), change the weighting of certain rules, or conduct other modifications.

Figure 3:
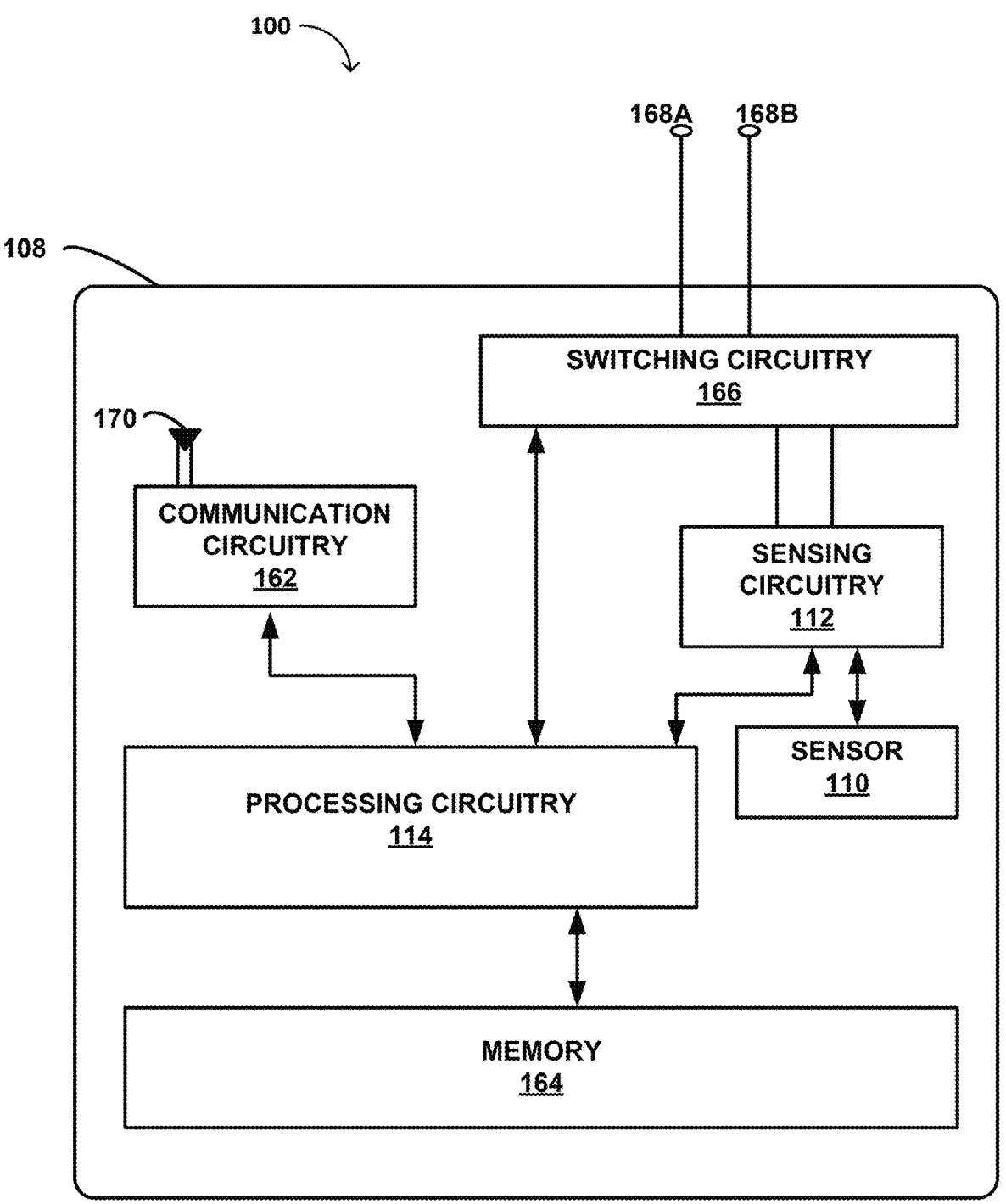
FIG. 3 is a block diagram illustrating circuitry of an example medical device.

FIG. 3 is a block diagram illustrating an example configuration of medical device 108. As shown in FIG. 3, medical device 108 may include at least some portion of processing circuitry 114, sensing circuitry 112, communication circuitry 162, memory 164, one or more sensors such as sensor 110, switching circuitry 166, and sensing element 168A, 168B (hereinafter "sensing elements 168"), one or more of which may be disposed on a housing of medical device 108. In some examples, memory 164 includes computer-readable instructions that, when executed by processing circuitry 114, cause medical device 108 and processing circuitry 114 to perform various functions attributed herein to medical device 108 and processing circuitry 114. Memory 164 may include any volatile, non-volatile, magnetic, optical, or electrical media, such as a random-access memory (RAM), ferro-electric RAM (F-RAM), read-only memory (ROM), non-volatile RAM (NVRAM), electrically-erasable programmable ROM (EEPROM), flash memory, or any other digital media. In examples, medical device 108 is an insertable cardiac monitor. Sensing element 168A may be a distal electrode. Sensing element 168B may be a proximal electrode.

Processing circuitry 114 may include fixed function circuitry and/or programmable processing circuitry. Processing circuitry 114 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 114 may include multiple components, such as any combination of one or more microprocessors, one or more controllers, one or more DSPs, one or more ASICs, or one or more FPGAs, as well as other discrete or integrated logic circuitry. The functions attributed to processing circuitry 114 herein may be embodied as software, firmware, hardware, or any combination thereof.

Sensing circuitry 112 may be selectively coupled to sensing elements 168 via switching circuitry 166 as controlled by processing circuitry 114. Sensing elements 168 may be configured to sense a patient physiological data of maternal patient 102 and/or a fetal physiological data of fetal patient 104, such as an electrocardiogram ("ECG"), echocardiogram, electromyography, impedance magnitude, optical signal, a pressure, an accelerometry, an audible sound, and/or any other physiological trait influenced by a body function of maternal patient 102 and/or the fetal patient 104. Sensing elements 158 may include, for example, electrodes, accelerometers, microphones, optical sensors, temperature sensors, force sensors, and/or pressure sensors. Sensing circuitry 112 may monitor signals from sensing elements 168 and provide an output signal to processing circuitry 114. Sensing circuitry 112 and/or processing circuitry 114 may include one or more filters and amplifiers for filtering and amplifying signals received from one or more of sensing elements 168 and/or other sensors. In some examples, sensing circuitry 112 and/or processing circuitry 114 may include a rectifier, filter and/or amplifier, a sense amplifier, comparator, and/or analog-to-digital converter. Processing circuitry 114 may define and/or monitor patient physiological data and/or fetal physiological data using the output signal and store the patient physiological data and/or fetal physiological data in memory 164.

Processing circuitry 114 may issue, via communication circuitry 162, a communication to patient IO device 118, external device 116, and/or clinician IO device 120, based on a comparison of a maternal attribute and a maternal limit and/or a comparison of a fetal attribute and a fetal limit. Processing circuitry 114 may communicate, via communication circuitry 162, at least a portion of the patient physiological data and/or the fetal physiological data to patient IO device 118, external device 116, and/or clinician IO device 120. Such transmissions may occur on a daily or other basis. Communication circuitry 162 may include any suitable hardware, firmware, software, or any combination thereof for communicating with another device, such as computing devices 12, with the aid of an internal or external antenna, e.g., antenna 170.

Medical device 108 may be any device configured to sense a maternal physiological trait and/or fetal physiological trait and communicate patient physiological data and/or fetal physiological data. In examples, medical device 108 may include a leadless, subcutaneously-implantable monitoring device configured to be implanted with maternal patient 102. Medical device 108 may be a device configured to substantially non-invasively contact a body of maternal patient 102 to position sensor 110 (e.g., smartwatch and/or other smart apparel). Medical device 108 may be a device configured to position sensor 110 through a manipulation by and/or action of maternal patient 102 (e.g., a weight scale, a blood pressure cuff, and/or a glucose testing device). Although described primarily in the context of examples in which medical device 108 takes the form of a device configured to be implanted within maternal patient 102, the medical device 108 may be any device configured to position sensor 110 such that sensor 110 may to sense a physiological trait of maternal patient 102 and/or fetal patient 104.

Figure 4:
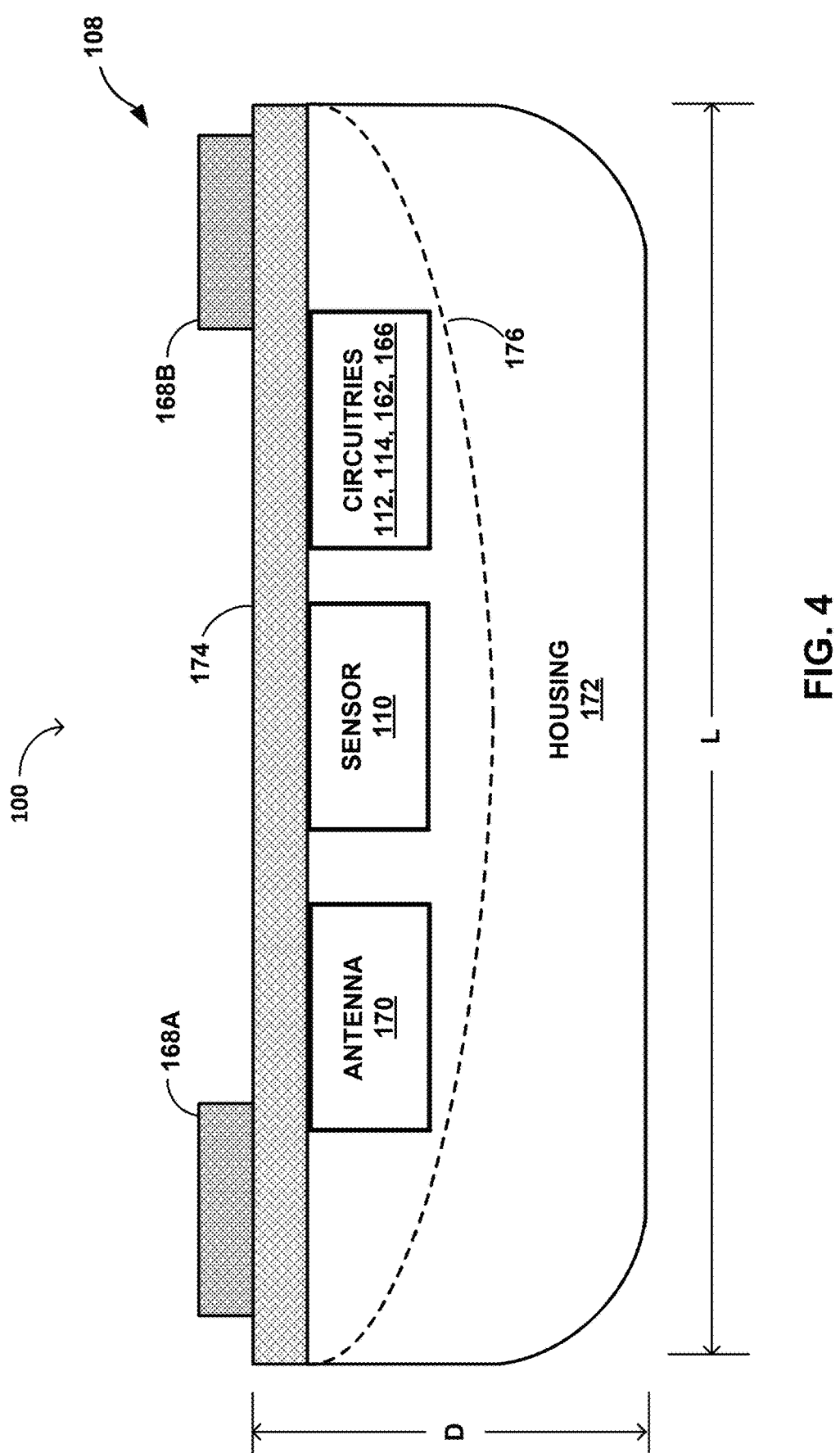
FIG. 4 is a schematic diagram illustrating an example medical device.

FIG. 4 is a conceptual side-view diagram illustrating an example configuration of medical device 108. In the example shown in FIG. 4, medical device 108 may include a housing 172 and a cover 174 mechanically supported by housing 172. Cover 174 may be an insulative cover. Sensing element 168A and sensing element 168B may be formed on or placed on an outer surface of cover 174, or otherwise in mechanical communication with cover 174. Circuitries 112, 114, 162, 166, described above with respect to FIGS. 1-3, may be formed on, placed within, and/or otherwise mechanically supported by an inner surface of cover 74, or within housing 72. Antenna 170 may be mechanically supported by, formed on, or placed within housing 172 and/or cover 174. In some examples, cover 74 may be positioned over an opening defined by housing 172, such that housing 172 and cover 174 enclose antenna 170, sensing elements 168, sensor 110, and/or circuitries 112, 114, 162, 166. Housing 172 and cover 174 may enclose antenna 170, sensing elements 168, sensor 110, and/or circuitries 112, 114, 162, 166 to, for example, protect antenna 170, sensing elements 168, sensor 110, and/or circuitries 112, 114, 162, 166 from fluids such as body fluids.

One or more of antenna 170, sensing elements 168, sensor 110, and/or circuitries 112, 114, 162, 166 may be formed on cover 174, such as by using flip-chip technology. Cover 174 may be flipped onto a housing 172. When flipped and placed onto housing 172, the components of medical device 108 formed on the inner side of cover 174 may be positioned in a gap 176 defined by housing 172. Sensing elements 168 may be electrically connected to switching circuitry 166 through one or more vias (not shown) formed through cover 174. Cover 174 may be formed of sapphire (i.e., corundum), glass, parylene, and/or any other suitable material. Housing 172 may be formed from titanium or any other suitable material (e.g., a biocompatible material). Sensing elements 168 (e.g., an electrode) may be formed from any of stainless steel, titanium, platinum, iridium, alloys thereof, or other suitable materials. In addition, sensing elements 168 may be coated with a material such as titanium nitride or fractal titanium nitride, although other suitable materials and coatings for such electrodes may be used.

In the example shown in FIG. 4, the housing 172 of medical device 108 defines a length L and a thickness or depth D and is in the form of an elongated rectangular prism wherein the length L is larger than the depth D. Housing 172 may define a width W perpendicular to the length L and perpendicular to the depth D (e.g. proceeding into the page). In examples, the width W is larger than the depth D. For example, the spacing between sensing element 168A and sensing element 168 B may range from 30 millimeters (mm) to 50 mm, from 35 mm to 45 mm, or be approximately 40 mm. In addition, in some examples, length L may range from 30 mm to about 70 mm. In other examples, the length L may range from 5 mm to 60 mm, 40 mm to 60 mm, 45 mm to 55 mm, or be approximately 45 mm. In addition, in examples, the width W may range from 3 mm to 15 mm, such as approximately 8 mm. In some examples, depth D may range from 2 mm to 15 mm, from 3 to 5 mm, or be approximately 4 mm. In some examples, medical device 108 may have a volume of three cubic centimeters (cm) or less, or 1.5 cubic cm or less, such as approximately 1.4 cubic cm.

Figure 5:
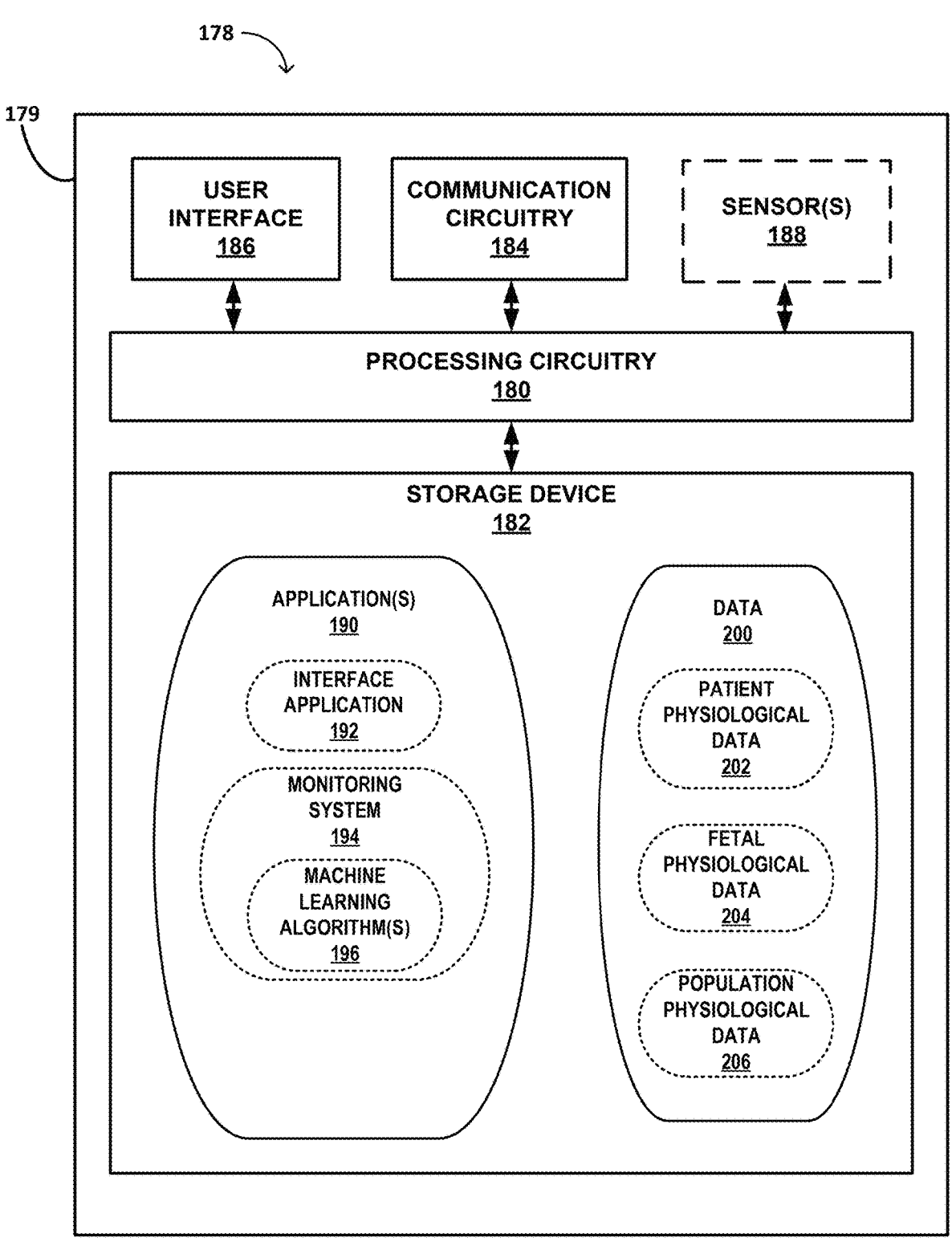
FIG. 5 is a block diagram illustrating an example configuration of a computing device that operates in accordance with one or more techniques of the present disclosure.

FIG. 5 is a block diagram illustrating an example configuration of a computing device 178 which may be an example of external device 116, clinician IO device 120, patient IO device 118, and/or medical devices 108, 122, 144, 150, 156. In some examples, computing device 178 takes the form of a smartphone, a laptop, a tablet computer, a personal digital assistant (PDA), a smartwatch or other wearable computing device, smart home appliance, such as a smart speaker, or any IoT device. As shown in the example of FIG. 5, computing device 178 includes processing circuitry 180, storage device 182, communication circuitry 184, a user interface 186 and, in some examples, one or more sensors 188. Processing circuitry 180 may include at least some portion of processing circuitry 114 (FIGS. 1-4). Storage device 182 may include at least some portion of memory 164 (FIG. 3). Communication circuitry 184 may include at least some portion of communication circuitry 162 (FIG. 3). Sensors 188 may include at least some portion of sensor 110 (FIG. 1-4). Although shown in FIG. 5 as a stand-alone device for purposes of example, computing device 178 may be any component or system that includes processing circuitry or other suitable computing environment for executing software instructions and, for example, need not necessarily include one or more elements shown in FIG. 5 (e.g., in some examples components such as storage device 182 may not be co-located or in the same chassis as other components).

Processing circuitry 180, in one example, is configured to implement functionality and/or process instructions for execution within computing device 178. For example, processing circuitry 180 may be capable of processing instructions, including applications 190, stored in storage device 182. Examples of processing circuitry 180 may include, any one or more of a microprocessor, a controller, a digital signal processor (DSP), an application specific integrated circuit (ASIC), a field-programmable gate array (FPGA), or equivalent discrete or integrated logic circuitry.

Storage device 182 may be configured to store information within computing device 178, including applications 190 and data 200. Data 200 may include patient physiological data 202, fetal physiological data 204, and/or population physiological data 206. Storage device 182, in some examples, is described as a computer-readable storage medium. In some examples, storage device 182 includes a temporary memory or a volatile memory. Examples of volatile memories include random access memories (RAM), dynamic random access memories (DRAM), static random access memories (SRAM), and other forms of volatile memories known in the art. Storage device 182, in one example, is used by applications 190 running on computing device 178 to temporarily store information during program execution. Storage device 182, in some examples, also includes one or more memories configured for long-term storage of information, e.g., including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 178 utilizes communication circuitry 184 to communicate with other devices, such as external device 116, clinician IO device 120, patient IO device 118, and/or medical device 108. Communication circuitry 184 may include a network interface card, such as an Ethernet card, an optical transceiver, a radio frequency transceiver, or any other type of device that can send and receive information. Other examples of such network interfaces may include 3G, 4G, 5G, and WiFi radios.

Computing device 178 also includes a user interface 186. User interface 186 may be configured to provide output to a user using tactile, audio, or video stimuli and receive input from a user through tactile, audio, or video feedback. User interface 186 may include, as examples, a presence-sensitive display, a mouse, a keyboard, a voice responsive system, video camera, microphone, or any other type of device for detecting a command from a user, a sound card, a video graphics adapter card, or any other type of device for converting a signal into an appropriate form understandable to humans or machines, a speaker, a cathode ray tube (CRT) monitor, a liquid crystal display (LCD), or any other type of device that can generate intelligible output to a user. In some examples, a presence-sensitive display includes a touch-sensitive screen.

Example applications 190 executable by processing circuitry 180 of computing device 178 may include an interface application 192 configured to facilitate a user interface with, for example, clinician IO device 120, patient IO device 118, external device 116, and/or medical device 108. Example applications 190 may include a monitoring system 194 that may utilize one or more machine learning algorithms 196. Execution of interface application 192 by processing circuitry 180 may configure computing device 178 to interface with clinician IO device 120, patient IO device 118, external device 116, and/or medical device 108. For example, interface application 192 may configure computing device 178 to communicate with clinician IO device 120, patient IO device 118, external device 116, and/or medical device 108 via communication circuitry 184. Processing circuitry 180 may receive patient physiological data 202 and/or fetal physiologic data 204 from medical device 108 and/or population physiological data 206 from medical devices 144, 150, 156, and store patient physiological data 202, fetal physiological data 204, and/or population physiological data in storage device 182. Interface 192 application may also configure user interface 186 for a user to interact with data 200, and/or interact with clinician IO device 120, patient IO device 118, external device 116, and/or medical device 108. Processing circuitry 180 may execute monitoring system 194 to facilitate monitoring the health of maternal patient 102 and/or fetal patient 104, e.g., based on data 200 and/or other data collected by computing device 178. Monitoring system 194 may cause processing circuitry 180 and computing device 178 to perform any of the techniques described herein related to the patient physiological data of maternal patient 102 and/or the fetal physiologic data of fetal patient 104.

In some examples, processing circuitry 180 executes monitoring system 194 to define a maternal attribute and/or fetal attribute. Processing circuitry 180 may execute monitoring system 194 to define and/or redefine a maternal limit and/or fetal limit. Processing circuitry 180 may execute monitoring system 194 to gather patient physiological data 202, fetal physiological data 204, and/or population physiological data 206. Processing circuitry 180 may execute monitoring system 194 define a patient parameter based on patient physiological data 202 and/or define a fetal parameter based on fetal physiological data 204. Processing circuitry 180 may execute monitoring system 194 to define a training data set and/or population training data set and train machine learning algorithm 196 using the training data set and/or population training data set. Processing circuitry 180 may execute monitoring system 194 to perform any of the techniques described herein for medical system 100.

In some examples, computing device 178 includes a housing 179 mechanically supporting and/or at least partially enclosing substantially all or at least some part of circuitry and/or other components configured to perform functions ascribed to processing circuitry 180, storage device 182, communication circuitry 184, user interface 186, sensors 188, applications 190, interface application 192, monitoring system 194, machine learning algorithms 196, data 200, patient physiological data 202, fetal physiological 204, and/or population physiological data 206.

Figure 6:
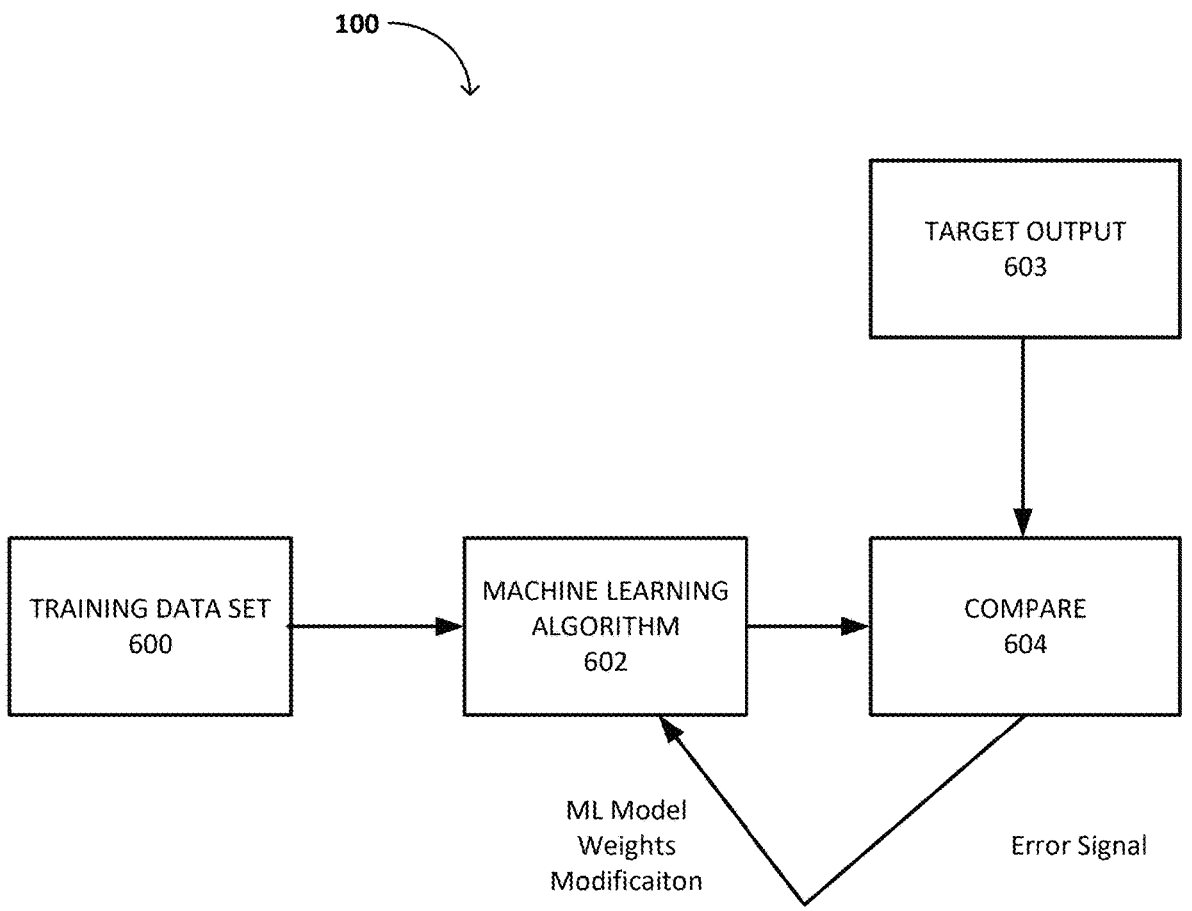
FIG. 6 is a conceptual diagram illustrating an example training process for a machine learning algorithm, in accordance with examples of the current disclosure.

FIG. 6 is an example of a machine learning algorithm 602 being trained using supervised and/or reinforcement learning techniques. The machine learning algorithm 602 may be implemented using any number of models for supervised and/or reinforcement learning, such as but not limited to, an artificial neural network, a decision tree, naïve Bayes network, support vector machine, or k-nearest neighbor model, to name only a few examples. In some examples, one or more of medical device 108, second medical device 122, processing circuitry 114, external device 116, clinician IO device 120, and/or patient input/output device 118 initially trains the machine learning algorithm 602 using a training data set 600. Training data set 600 may include training input vectors indicative of patient physiological data and/or fetal physiological data, wherein one or more elements in a training input vector may be representative of maternal physiological traits, maternal attributes, fetal physiological traits, fetal attributes, and/or other maternal physiological data and/or fetal physiological data. In examples, training data set 600 includes population input vectors indicative of population physiological data, wherein one or more elements in a population input vector may be representative of physiological traits and/or attributes of other individual prenatal patients carrying other fetal patients. Each of the training input vectors and/or each of the population input vectors may be associated with a training output vector to define a data pair.

One or more of medical device 108, second medical device 122, processing circuitry 114, external device 116, clinician IO device 120, and/or patient input/output device 118 may select training data set 600 comprising a set of data pairs. A prediction by the machine learning algorithm 602 may be compared 604 to a target output 603 (e.g., a target output described by a training output vector), and an error signal and/or machine learning model weights modification may sent/applied to machine learning algorithm 602 based on the comparison to modify/update machine learning model 602. For example, one or more of medical device 108, second medical device 122, processing circuitry 114, external device 116, clinician IO device 120, and/or patient input/output device 118 may, for each training instance in the training set, modify machine learning model 602 to change a score generated by machine learning model 602 in response to subsequent input vectors applied to machine learning algorithm 602. In examples, the error signal and/or machine learning model weights modification modifies and/or alters the mapping of a subsequent training vector onto an output space defined by one or more training output vectors.

Figure 7:
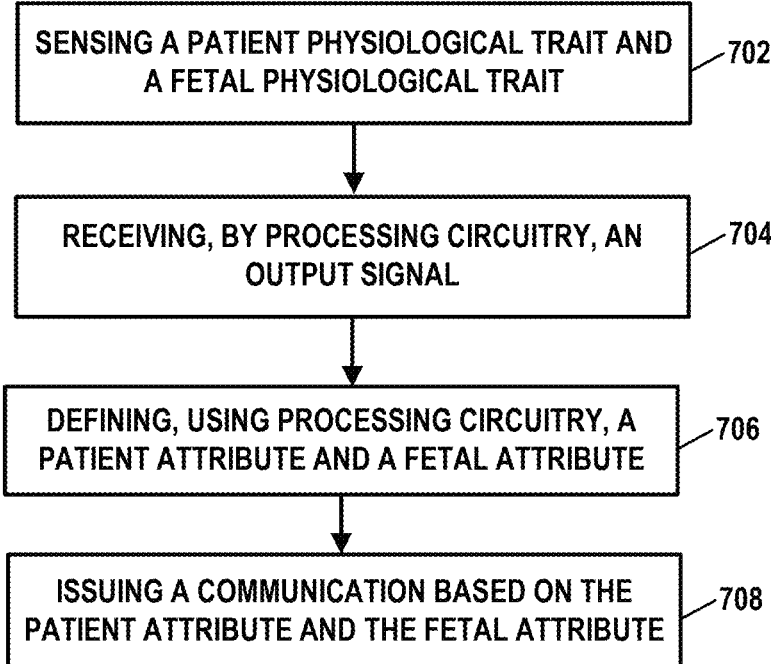
FIG. 7 is a flow diagram illustrating an example technique for monitoring a physiological trait of a maternal patient and a fetal patient carried by the maternal patient.

FIG. 7 is a flow diagram illustrating an example technique for sensing physiological attributes of a patient and a fetal patient to monitor a pregnancy. Although the technique is described mainly with reference to medical system 100 of FIGS. 1-6, the technique may be performed by other medical systems in other examples.

The technique includes sensing a maternal physiological trait and a fetal physiological trait using one or more sensors 110, 124, 188 (702). The maternal physiological trait is indicative of a maternal attribute of maternal patient 102. The fetal physiological is indicative of a fetal attribute of fetal patient 104 carried by maternal patient 102. The maternal attribute is indicative of a physiological characteristic of a body of maternal patient 102 and the fetal attribute is indicative of a physiological characteristic of a body of fetal patient 104. In examples, the maternal attribute is at least one of a heartrate of maternal patient 102, a systolic blood pressure of maternal patient 102, a diastolic blood pressure of maternal patient 102, an oxygen saturation level of maternal patient 102, a respiration rate of maternal patient 102, a temperature of maternal patient 102, a muscular contraction of maternal patient 102, a blood glucose level of maternal patient 102, and/or a weight of maternal patient 102. In examples, the fetal attribute is at least one of a heartrate of fetal patient 104, a systolic blood pressure of fetal patient 104, a diastolic blood pressure of fetal patient 104, an oxygen saturation level of fetal patient 104, a respiration rate of fetal patient 104, and/or a temperature of fetal patient 104.

The maternal physiological trait sensed may be an electrocardiogram of maternal patient 102, an echocardiogram of maternal patient 102, an audible sound generated by maternal patient 102, an accelerometer signal indicative of a movement of maternal patient 102, an electromyography signal indicative of a muscle contraction of maternal patient 102, an oxygen saturation signal indicative of an oxygen saturation of maternal patient 102, an optical signal influenced by the body of maternal patient 102, and/or another maternal physiological trait. The fetal physiological trait sensed may be an electrocardiogram of fetal patient 104, an echocardiogram of fetal patient 104, an audible sound generated by fetal patient 104, an accelerometer signal indicative of a movement of fetal patient 104, an electromyography signal indicative of a muscle contraction of fetal patient 104, an oxygen saturation signal indicative of an oxygen saturation of fetal patient 104, an optical signal influenced by the body of fetal patient 104, and/or another fetal physiological trait. In some examples, sensors 110, 124, 188 sense a mixed physiological trait indicative of both the maternal attribute and the fetal attribute. In some examples, sensors 110, 124, 188 sense the patient physiological attribute using a first sensor and sense the fetal physiological attribute using a second sensor.

The technique includes receiving, by processing circuitry 114, 180 an output signal 134 generated by sensing circuitry 112, 126, operably coupled to sensors 110, 124, 188 (704). Output signal 134 is indicative of the maternal attribute and the fetal attribute. The technique includes defining, using processing circuitry 114, 180 the maternal attribute and the fetal attribute using output signal 134 (706). In examples, output signal 134 includes a first output signal indicative of the maternal attribute and a second output signal indicative of the fetal attribute, and processing circuitry 114, 180 defines the maternal attribute using the first output signal and defines the fetal attribute using the second output signal. In examples, output signal 134 includes a mixed output signal indicative of both the maternal attribute and the fetal attribute, and processing circuitry 114, 180 defines the maternal attribute and the fetal attribute using the mixed output signal. Processing circuitry 114, 180 may perform a signal separation technique to define the maternal attribute and the fetal attribute.

The technique includes issuing a communication, using processing circuitry 114, 180 based on at least one of a comparison of the maternal attribute and a maternal limit or a comparison of the fetal attribute and a fetal limit (708). Processing circuitry 114, 180 may convey the communication using communications circuitry 162, 184. Processing circuitry 114, 180 may issue the communication to device circuitry of at least one of patient input/output device 118, external device 116, and/or clinician IO device 120. In examples, processing circuitry 114, 180 communicates data indicative of at least one of the maternal physiological trait, a patient physiological parameter indicative of the maternal physiological trait, the maternal attribute, the fetal physiological trait, a fetal physiological parameter indicative of the fetal physiological trait, or the fetal attribute to device circuitry of at least one of a patient input/output device 118, external device 116, and/or clinician IO device 120.

Processing circuitry 114, 180 may compare the maternal attribute to a maternal limit which describes a threshold for a specific condition of patient 102. In examples, the maternal attribute is indicative of a heartrate of patient 102 and the specific condition of patient 102 is one of a maximum heartrate of patient 102 or a minimum heart rate of patient 102. In examples, the maternal attribute is indicative of a systolic blood pressure of patient 102 and the specific condition of patient 102 is one of a maximum systolic blood pressure of patient 102 or a minimum systolic blood pressure of patient 102. In examples, the maternal attribute is indicative of a diastolic blood pressure of patient 102 and the specific condition of the patient is one of a maximum diastolic blood pressure of patient 102 or a minimum diastolic blood pressure of patient 102. In examples, the maternal attribute is indicative of an oxygen saturation level of patient 102 and the specific condition of the patient is one of a maximum oxygen saturation level of patient 102 or a minimum oxygen saturation level of patient 102. In examples, the maternal attribute is indicative of a respiration rate of patient 102 and the specific condition of patient 102 is one of a maximum respiration rate of patient 102 or a minimum respiration rate of patient 102. In examples, the maternal attribute is indicative of a temperature of the patient and the specific condition of patient 102 is one of a maximum temperature of patient 102 or a minimum temperature of patient 102. In examples, the maternal attribute is indicative of an activity level of patient 102 and the specific condition of patient 102 is one of a maximum activity level of patient 102 or a minimum activity level of patient 102. In examples, the maternal attribute is indicative of a muscular contraction of patient 102 and the specific condition of patient 102 is one of false labor or maternal labor. In examples, the maternal attribute is indicative of a blood glucose level of patient 102 and the specific condition of patient 102 is one of a maximum blood glucose level of patient 102 or a minimum blood glucose level of patient 102. In examples, the maternal attribute is indicative of a weight of patient 102 and the specific condition of patient 102 is one of a maximum weight of patient 102 or a minimum weight of patient 102.

Processing circuitry 114, 180 may compare the fetal attribute to a fetal limit which describes a threshold for a specific condition of fetal patient 104. In examples, the fetal attribute is indicative of a heartrate of fetal patient 104 and the specific condition of fetal patient 104 is one of a maximum heartrate of fetal patient 104 or a minimum heart rate of fetal patient 104. In examples, the fetal attribute is indicative of a systolic blood pressure of fetal patient 104 and the specific condition of fetal patient 104 is one of a maximum systolic blood pressure of fetal patient 104 or a minimum systolic blood pressure of fetal patient 104. In examples, the fetal attribute is indicative of a diastolic blood pressure of fetal patient 104 and the specific condition of fetal patient 104 is one of a maximum diastolic blood pressure of fetal patient 104 or a minimum diastolic blood pressure of fetal patient 104. In examples, the fetal attribute is indicative of an oxygen saturation level of fetal patient 104 and the specific condition of fetal patient 104 is one of a maximum oxygen saturation level of fetal patient 104 or a minimum oxygen saturation level of fetal patient 104. In examples, the fetal attribute is indicative of a respiration rate of fetal patient 104 and the specific condition of fetal patient 104 is one of a maximum respiration rate of fetal patient 104 or a minimum respiration rate of fetal patient 104. In examples, the fetal attribute is indicative of a temperature of fetal patient 104 and the specific condition of fetal patient 104 is one of a maximum temperature of fetal patient 104 or a minimum temperature of fetal patient 104. In examples, the fetal attribute is indicative of an activity level of fetal patient 104 and the specific condition of fetal patient 104 is one of a maximum activity level of fetal patient 104 or a minimum activity level of fetal patient 104.

In examples, processing circuitry 114, 180 issues the communication using a tiered communication indicative of an assessment of the comparison of the maternal attribute and the maternal limit and/or the comparison of the fetal attribute and the fetal limit. Processing circuitry 114, 180 may define a tier of a communication based on a plurality of maternal limits (e.g., a first maternal limit, a second maternal limit, and/or a third maternal limit) and/or a plurality of fetal limits (e.g., a first fetal limit, a second fetal limit, and/or a third fetal limit). In examples, processing circuitry 114, 180 issues a Tier I communication when the maternal attribute and/or fetal attribute are assessed to be a normally expected value (e.g., within a range defined by the first maternal limit and/or the first fetal limit). Processing circuitry 114, 180 may issue a Tier II communication when the maternal attribute and/or fetal attribute are assessed to potentially indicate a condition warranting further evaluation and/or action by maternal patient 102 and/or a clinician (e.g., within a range defined by the second maternal limit and/or the second fetal limit.) Processing circuitry 114, 180 may issue a Tier III communication when the maternal attribute and/or fetal attribute are assessed to indicate a condition potentially more serious and/or warranting more urgent action and/or action by maternal patient 102 and/or the clinician (e.g., within a range defined by the third maternal limit and/or the third fetal limit).

The tiered communication system may define any number of tiers and any number of maternal limits and/or fetal limits. In some examples, processing circuitry 114 causes patient IO device 118 and/or clinician IO device 120 to provide visible, audible, or other indicia associated with a tier of the communication. For example, processing circuitry 114 may cause patient IO device 118 and/or clinician IO device 120 to provide a first indicia (e.g., a green background) for a Tier I communication, a second indicia (e.g., a yellow background) for a Tier II communication, and/or a third indicia (e.g., a red background) for a Tier III communication. In examples, processing circuitry 114, 180 may select and/or communicate one or more treatment recommendations based on the communication.

Processing circuitry 114, 180 may define and/or refine the maternal limit and/or fetal limit to reduce a rate of false positives when comparing the maternal attribute to the maternal limit and/or the fetal attribute to the fetal limit.

Processing circuitry 114, 180 may utilize patient physiological data to define and/or refine the maternal limit. Processing circuitry 114, 180 may utilize fetal physiological data to define and/or refine the fetal limit. In examples, processing circuitry 114, 180 uses a machine learning algorithm 196 trained with a training data set based on the patient physiological data and/or the fetal physiological data. Machine learning algorithm 196 may define and/or refine the maternal limit using the patient physiological data and/or define and/or refine the fetal limit using the fetal physiological data. In examples, medical system 100 receives an assessment input from patient input/output device 118, external device 116, and/or clinician IO device 120, or another input device. Machine learning algorithm 196 may be trained using a training data set including the assessment input.

In some examples, processing circuitry 114, 180 may define and/or refine the maternal limit and/or fetal limit based on population data sensed from a population of other individual prenatal patients 148, 154, 160. Processing circuitry 114, 180 may utilize machine learning algorithm 196 to define and/or refine the maternal limit and/or fetal limit using the population data. Processing circuitry 114, 180 may communicate with individual medical devices 144, 150, 156 to gather the population data.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The disclosure includes the following examples.

Example 1: A system comprising: one or more sensors configured to sense a maternal physiological trait indicative of a maternal attribute of a maternal patient and a fetal physiological trait indicative of a fetal attribute of a fetal patient carried by the maternal patient, wherein the maternal attribute is indicative of a physiological characteristic of a body of the maternal patient and the fetal attribute is indicative of a physiological characteristic of a body of the fetal patient; sensing circuitry operably coupled to the one or more sensors and configured to issue an output signal indicative of the maternal physiological trait and the fetal physiological trait; and processing circuitry operably connected to the sensing circuitry, wherein the processing circuitry is configured to: receive the output signal from the sensing circuitry, define the maternal attribute and the fetal attribute for the received output signal, and issue a communication based on at least one of: a comparison of the maternal attribute and a maternal limit, wherein the maternal limit defines a threshold for the maternal attribute, or a comparison of the fetal attribute and a fetal limit, wherein the fetal limit defines a threshold for the fetal attribute.

Example 2: The system of example 1, wherein: the one or more sensors are configured to sense a mixed physiological trait indicative of the maternal physiological trait and the fetal physiological trait, the output signal is indicative of the mixed physiological trait, and the processing circuitry is configured to separate the output signal into the maternal attribute and the fetal attribute.

Example 3: The system of example 1 or example 2, wherein: the one or more sensors includes at least a first sensor and a second sensor, the first sensor is configured to sense the maternal physiological trait, the second sensor is configured to sense the fetal physiological trait, the output signal includes a first output signal from first sensing circuitry of the first sensor and a second output signal from second sensing circuitry of the second sensor, and the processing circuitry is configured to define the maternal attribute using the first output signal and define the fetal attribute using the second output signal.

Example 4: The system of any of examples 1-3, wherein: the maternal attribute is at least one of a heartrate of the maternal patient, a systolic blood pressure of the maternal patient, a diastolic blood pressure of the maternal patient, an oxygen saturation level of the maternal patient, a respiration rate of the maternal patient, a temperature of the maternal patient, a muscular contraction of the maternal patient, a blood glucose level of the maternal patient, or a weight of the maternal patient.

Example 5: The system of any of examples 1-4, wherein: the fetal attribute is at least one of a heartrate of the fetal patient, a systolic blood pressure of the fetal patient, a diastolic blood pressure of the fetal patient, an oxygen saturation level of the fetal patient, a respiration rate of the fetal patient, or a temperature of the fetal patient.

Example 6: The system of any of examples 1-5, wherein: the processing circuitry is configured to receive a designated start of a pregnancy of the maternal patient as an input from a user input device, the processing circuitry is configured to determine an elapsed time since the designated start of the pregnancy, and the processing circuitry is configured to select the maternal limit and the fetal limit based the elapsed time.

Example 7: The system of any of examples 1-6, wherein the one or more sensors are configured to sense a first physiological trait indicative of a first maternal attribute and a second physiological trait indicative of a second maternal attribute, and wherein the maternal attribute is based on at least the first maternal attribute and the second maternal attribute.

Example 8: The system of any of examples 1-7, wherein the processing circuitry is configured to generate a plurality of individual maternal attributes as the processing circuitry receives the output signal, and wherein the maternal attribute is based on the plurality of individual maternal attributes.

Example 9: The system of any of examples 1-8, wherein the one or more sensors are configured to sense a first physiological trait indicative of a first fetal attribute and a second physiological characteristic indicative of a second fetal attribute, and wherein the fetal attribute is based on at least the first physiological trait and the second physiological trait.

Example 10: The system of any of examples 1-9, wherein the processing circuitry is configured to generate a plurality of individual fetal attributes as the processing circuitry receives the output signal, and wherein the fetal limit is based on the plurality of individual fetal attributes.

Example 11: The system of any of examples 1-10, wherein the processing circuitry is configured to issue the communication to device circuitry of a patient input/output device to cause the patient input/output device to provide an output sensible by the maternal patient, a clinician, or another user when the processing circuitry issues the communication.

Example 12: The system of any of examples 1-11, wherein the processing circuitry is configured to communicate physiological data indicative of at least one of the maternal physiological trait, the maternal attribute, the fetal physiological trait, or the fetal attribute to device circuitry of a patient input/output device.

Example 13: The system of any of examples 1-12, wherein the processing circuitry is configured to communicate physiological data indicative of at least one of the maternal physiological trait, the maternal attribute, the fetal physiological trait, or the fetal attribute to device circuitry of at least one of a clinician input/output device or an external device communicatively coupled to the clinician input/output device.

Example 14: The system of any of examples 1-13, wherein the processing circuitry is configured to generate a plurality of maternal attributes as the processing circuitry receives the output signal, and wherein the processing circuitry is configured to define the maternal limit using the plurality of maternal attributes.

Example 15: The system of any of examples 1-14, wherein the processing circuitry is configured to generate a plurality of fetal attributes as the processing circuitry receives the output signal, and wherein the processing circuitry is configured to define the fetal limit using the plurality of fetal attributes.

Example 16: The system of any of examples 1-15, wherein the sensor and at least some portion of the sensing circuitry are mechanically supported by a housing of a medical device, and wherein at least some portion of the processing circuitry is mechanically supported by a housing of an external device, wherein the housing of the medical device is displaced from the housing of the external device.

Example 17: The system of any of examples 1-16, further comprising a medical device configured to contact a body of the maternal patient, wherein the medical device mechanically supports the sensor and at least some portion of the sensing circuitry.

Example 18: The system of example 17, wherein the medical device is an implantable medical device configured to implant within the body of the maternal patient.

Example 19: The system of example 17 or example 18, wherein the medical device mechanically supports at least some portion of the processing circuitry.

Example 20: The system of any of examples 1-19, wherein the processing circuitry is configured to select treatment recommendations based on the communication.

Example 21: The system of example 20, wherein the processing circuitry is configured to communicate the treatment recommendations to device circuitry mechanically supported by a patient input/output device to cause the patient input/output device to provide an output sensible by the maternal patient, a clinician, or another user indicative of the treatment recommendations.

Example 22: The system of examples 1-21, wherein the maternal limit comprises a plurality of individual maternal limits and the fetal limit comprises a plurality of individual fetal limits, and wherein the processing circuitry is configured to issue the communication based on at least one of: a comparison of the maternal attribute and an individual maternal limit, wherein the communication is indicative of the individual maternal limit, or a comparison of the fetal attribute and an individual fetal limit, wherein the communication is indicative of the individual maternal limit.

Example 23: The system of example 22, wherein the processing circuitry is configured to: issue a tier I patient communication based on a comparison of the maternal attribute and a first maternal limit, issue a tier II patient communication based on a comparison of the maternal attribute and a second maternal limit, and issue a tier III patient communication based on a comparison of the maternal attribute and a third maternal limit, and issue a tier I fetal communication based on a comparison of the fetal attribute and a first fetal limit, issue a tier II fetal communication based on a comparison of the fetal attribute and a second fetal limit, and issue a tier III fetal communication based on a comparison of fetal attribute and a third fetal limit.

Example 24: The system of example 23, wherein the processing circuitry is configured to issue at least one of the tier I patient communication, the tier II patient communication, the tier III patient communication, the tier I fetal communication, the tier II fetal communication, or the tier III fetal communication to device circuitry of a patient input/output device.

Example 25: The system of example 23 or example 24, wherein the processing circuitry is configured to issue at least one of the tier I patient communication, the tier II patient communication, the tier III patient communication, the tier I fetal communication, the tier II fetal communication, or the tier III fetal communication to device circuitry of an external device.

Example 26: The system of any of examples 1-25, wherein the processing circuitry is configured to at least one of: compare the maternal attribute to the maternal limit using a machine learning algorithm, or compare the fetal attribute to the fetal limit using the machine learning algorithm.

Example 27: The system of example 26, wherein the processing circuitry is configured to receive an input from a clinician input/output device, wherein the input is indicative of an assessed risk to the maternal patient when the processing circuitry issued a previously issued communication and a previously defined maternal attribute, and wherein the machine learning algorithm is trained using a training data set indicative of the previously defined maternal attribute and the indicative input.

Example 28: The system of example 27, wherein the processing circuitry is configured to update the training set of the machine learning algorithm based on the maternal attribute.

Example 29: The system of example 27 or example 28, wherein the processing circuitry is configured to update the training set of the machine learning algorithm based on the indicative input.

Example 30: The system of any of examples 27-29, wherein the processing circuitry is configured to receive the input from the clinician input/output device, wherein the input is indicative of an assessed risk to the fetal patient when the processing circuitry issued a previously issued communication and a previously defined fetal attribute, and wherein the machine learning algorithm is trained using a training data set indicative of the previously defined fetal attribute and the indicative input.

Example 31: The system of example 30, wherein the processing circuitry is configured to update the training set of the machine learning algorithm based on the fetal attribute.

Example 32: The system of example 30 or example 31, wherein the processing circuitry is configured to update the training set of the machine learning algorithm based on the indicative input.

Example 33: The system any of examples 1-32, wherein the processing circuitry is configured to receive an input from a clinician input/output device, wherein the input is indicative of an assessed risk to the maternal patient when the processing circuitry issued a previously issued communication and a previously defined maternal attribute, and define the maternal limit using a machine learning algorithm, wherein the machine learning algorithm is trained using a training data set indicative of the previously defined maternal attribute and the indicative communication.

Example 34: The system any of examples 1-33, wherein the processing circuitry is configured to receive an input from a clinician input/output device, wherein the input is indicative of an assessed risk to the fetal patient when the processing circuitry issued a previously issued communication and a previously defined fetal attribute, and wherein the processing circuitry is configured to define the fetal limit using a machine learning algorithm, wherein the machine learning algorithm is trained using a training data set indicative of the previously defined fetal attribute and the indicative communication.

Example 35: The system of any of examples 1-34, wherein the processing circuitry is configured to define the maternal limit using a machine learning algorithm, wherein the machine learning algorithm is trained using maternal attributes sensed from a population of other patients carrying a fetal patient.

Example 36: The system of any of examples 1-35, wherein the processing circuitry is configured to define the fetal limit using a machine learning algorithm, wherein the machine learning algorithm is trained using fetal attributes sensed from a population of other fetal patients carried by other patients.

Example 37: The system of any of examples 1-36, wherein: the one or more sensors includes a sensor mechanically supported by a first housing and a sensor mechanically supported by a second housing, and the first housing is configured to contact a body of the maternal patient at a first anatomical location and the second housing is configured to contact the body of the maternal patient at second anatomical location.

Example 38: The system of examples 1-37, wherein the processing circuitry is configured to at least one of: compare the maternal attribute to the maternal limit, wherein the maternal limit describes a threshold for a specific condition of the maternal patient, or compare the fetal attribute to the fetal limit, wherein the fetal limit describes a threshold for a specific condition of the fetal patient.

Example 39: The system of example 38, wherein the processing circuitry is configured to issue the communication based on at least one of: the comparison of the maternal attribute and the maternal limit, wherein the maternal attribute is indicative of a heartrate of the maternal patient, and wherein the specific condition of the maternal patient is one of a maximum heartrate of the maternal patient or a minimum heart rate of the maternal patient, or the comparison of the fetal attribute and the fetal limit, wherein the fetal attribute is indicative of a heartrate of the fetal patient, and wherein the specific condition of the fetal patient is one of a maximum heartrate of the fetal patient or a minimum heart rate of the fetal patient.

Example 40: The system of example 38 or example 39, wherein the processing circuitry is configured to issue the communication based on at least one of: the comparison of the maternal attribute and the maternal limit, wherein the maternal attribute is indicative of a systolic blood pressure of the maternal patient, and wherein the specific condition of the maternal patient is one of a maximum systolic blood pressure of the maternal patient or a minimum systolic blood pressure of the maternal patient, or the comparison of the fetal attribute and the fetal limit, wherein the fetal attribute is indicative of a systolic blood pressure of the fetal patient, and wherein the specific condition of the fetal patient is one of a maximum systolic blood pressure of the fetal patient or a minimum systolic blood pressure of the fetal patient.

Example 41: The system of any of examples 38-40, wherein the processing circuitry is configured to issue the communication based on at least one of: the comparison of the maternal attribute and the maternal limit, wherein the maternal attribute is indicative of a diastolic blood pressure of the maternal patient, and wherein the specific condition of the maternal patient is one of a maximum diastolic blood pressure of the maternal patient or a minimum diastolic blood pressure of the maternal patient, or the comparison of the fetal attribute and the fetal limit, wherein the fetal attribute is indicative of a diastolic blood pressure of the fetal patient, and wherein the specific condition of the fetal patient is one of a maximum diastolic blood pressure of the fetal patient or a minimum diastolic blood pressure of the fetal patient.

Example 42: The system of any of examples 38-41, wherein the processing circuitry is configured to issue the communication based on at least one of: the comparison of the maternal attribute and the maternal limit, wherein the maternal attribute is indicative of an oxygen saturation level of the maternal patient, and wherein the specific condition of the maternal patient is one of a maximum oxygen saturation level of the maternal patient or a minimum oxygen saturation level of the maternal patient, or the comparison of the fetal attribute and the fetal limit, wherein the fetal attribute is indicative of an oxygen saturation level of the fetal patient, and wherein the specific condition of the fetal patient is one of a maximum oxygen saturation level of the fetal patient or a minimum oxygen saturation level of the fetal patient.

Example 43: The system of any of examples 38-42, wherein the processing circuitry is configured to issue the communication based on at least one of: the comparison of the maternal attribute and the maternal limit, wherein the maternal attribute is indicative of a respiration rate of the maternal patient, and wherein the specific condition of the maternal patient is one of a maximum respiration rate of the maternal patient or a minimum respiration rate of the maternal patient, or the comparison of the fetal attribute and the fetal limit, wherein the fetal attribute is indicative of a respiration rate of the fetal patient, and wherein the specific condition of the fetal patient is one of a maximum respiration rate of the fetal patient or a minimum respiration rate of the fetal patient.

Example 44: The system of any of examples 38-43, wherein the processing circuitry is configured to issue the communication based on at least one of: the comparison of the maternal attribute and the maternal limit, wherein the maternal attribute is indicative of a temperature of the maternal patient, and wherein the specific condition of the maternal patient is one of a maximum temperature of the maternal patient or a minimum temperature of the maternal patient, or the comparison of the fetal attribute and the fetal limit, wherein the fetal attribute is indicative of a temperature of the fetal patient, and wherein the specific condition of the fetal patient is one of a maximum temperature of the fetal patient or a minimum temperature of the fetal patient.

Example 45: The system of any of examples 38-44, wherein the processing circuitry is configured to issue the communication based on at least one of: the comparison of the maternal attribute and the maternal limit, wherein the maternal attribute is indicative of an activity level of the maternal patient, and wherein the specific condition of the maternal patient is one of a maximum activity level of the maternal patient or a minimum activity level of the maternal patient, or the comparison of the fetal attribute and the fetal limit, wherein the fetal attribute is indicative of an activity level of the fetal patient, and wherein the specific condition of the fetal patient is one of a maximum activity level of the fetal patient or a minimum activity level of the fetal patient.

Example 46: The system of any of examples 38-45, wherein the maternal attribute is indicative of a muscular contraction of the maternal patient, and wherein the specific condition of the maternal patient is one of false labor or maternal labor.

Example 47: The system of any of examples 38-46, wherein the maternal attribute is indicative of a level of amniotic fluid of the maternal patient, and wherein the specific condition of the maternal patient is one of minimum amniotic fluid level or a maximum amniotic fluid level.

Example 48: The system of any of examples 38-47, wherein the maternal attribute is indicative of a blood glucose level of the maternal patient, and wherein the specific condition of the maternal patient is one of a maximum blood glucose level of the maternal patient or a minimum blood glucose level of the maternal patient.

Example 49: The system of any of examples 38-48, wherein the maternal attribute is indicative of a weight of the maternal patient, and wherein the specific condition of the maternal patient is one of a maximum weight of the maternal patient or a minimum weight of the maternal patient.

Example 50: The system of any of examples 1-49, wherein the patient physiological characteristic comprises an electrocardiogram of a heart of the maternal patient.

Example 51: The system of any of examples 1-50, wherein the one or more sensors are configured to sense the parent physiological trait and the fetal physiological trait by sensing at least one of an electrocardiogram of the maternal patient or an electrocardiogram of the fetal patient.

Example 52: The system of any of examples 1-51, wherein the one or more sensors are configured to sense the parent physiological trait and the fetal physiological trait by sensing at least one of an echocardiogram of the maternal patient or an echocardiogram of the fetal patient.

Example 53: The system of any of examples 1-52, wherein the one or more sensors are configured to sense the parent physiological trait and the fetal physiological trait by sensing at least one of an audible sound generated by a body of the maternal patient an audible sound generated by a body of the fetal patient.

Example 54: The system of any of examples 1-53, wherein the one or more sensors are configured to sense the parent physiological trait and the fetal physiological trait by sensing at least one of an accelerometer motion caused by a physical movement of the maternal patient or an accelerometer motion caused by a physical movement of the fetal patient.

Example 55: The system of any of examples 1-54, wherein the one or more sensors are configured to sense the parent physiological trait and the fetal physiological trait by sensing at least one of an electromyograph signal of the maternal patient or an electromyograph signal of the fetal patient.

Example 56: The system of any of examples 1-55, wherein the one or more sensors are configured to sense the parent physiological trait and the fetal physiological trait by sensing at least one of an oxygen saturation signal of the maternal patient or an oxygen saturation signal of the fetal patient.

Example 57: The system of any of examples 1-56, wherein the one or more sensors are configured to sense the parent physiological trait and the fetal physiological trait by sensing at least one of an optical signal influenced by the maternal patient or an optical signal influenced by the fetal patient.

Example 58: The system of any of examples 1-57, wherein the one or more sensors are configured to sense the parent physiological trait and the fetal physiological trait by sensing at least one of an arterial tonometry signature of the maternal patient or an arterial tonometry signature of the fetal patient.

Example 59: The system of any of examples 1-58, wherein the one or more sensors are configured to sense the parent physiological trait and the fetal physiological trait by sensing a force exerted by a weight of the maternal patient.

Example 60: The system of any of examples 1-59, wherein the one or more sensors are configured to sense the parent physiological trait and the fetal physiological trait by sensing at least one of a blood glucose level of the maternal patient.

Example 61. A method, comprising: sensing a maternal physiological trait indicative of a maternal attribute of a maternal patient and a fetal physiological trait indicative of a fetal attribute of a fetal patient carried by the maternal patient using one or more sensors, wherein the maternal attribute is indicative of a physiological characteristic of a body of the maternal patient and the fetal attribute is indicative of a physiological characteristic of a body of the fetal patient; receiving, by processing circuitry, an output signal generated by sensing circuitry operably coupled to the one or more sensors, wherein the output signal is indicative of the maternal attribute and the fetal attribute, defining, using the processing circuitry, the maternal attribute and the fetal attribute using the output signal, and issuing a communication, using the processing circuitry, a communication based on at least one of: a comparison of the maternal attribute and a maternal limit, wherein the maternal limit defines a threshold for the maternal attribute, or a comparison of the fetal attribute and a fetal limit, wherein the fetal limit defines a threshold for the fetal attribute.

Example 62: The method of example 61, further comprising: sensing, using the one or more sensors, a mixed physiological trait indicative of both the maternal attribute and the fetal attribute, separating, using the processing circuitry, the output signal into the maternal attribute and the fetal attribute, wherein the output signal is indicative of the mixed physiological trait.

Example 63: The method of example 61 or example 62, further comprising: sensing, using a first sensor of the one or more sensors, the maternal physiological trait, sensing, using a second sensor of the one or more sensors, the fetal physiological trait, generating, by the sensing circuitry, a first output signal indicative of the maternal attribute and a second output indicative of the fetal attribute, and defining, using the processing circuitry, the maternal attribute using the first output signal and the fetal attribute using the second output signal.

Example 64: The method of any of examples 61-63, wherein the maternal attribute at least one of a heartrate of the maternal patient, a systolic blood pressure of the maternal patient, a diastolic blood pressure of the maternal patient, an oxygen saturation level of the maternal patient, a respiration rate of the maternal patient, a temperature of the maternal patient, a muscular contraction of the maternal patient, a blood glucose level of the maternal patient, or a weight of the maternal patient.

Example 65: The method of any of examples 61-64, wherein the fetal attribute is at least one of a heartrate of the fetal patient, a systolic blood pressure of the fetal patient, a diastolic blood pressure of the fetal patient, an oxygen saturation level of the fetal patient, a respiration rate of the fetal patient, or a temperature of the fetal patient.

Example 66: The method of any of examples 61-65, further comprising: receiving, by the processing circuitry, a designated start of a pregnancy of the maternal patient as an input from a user input device, determining, by the processing circuitry an elapsed time since the designated start of the pregnancy, and selecting, by the processing circuitry, the maternal limit and the patient fetal limit based the elapsed time.

Example 67: The method of any of examples 61-66, further comprising: sensing, using the one or more sensors, a first physiological trait indicative of a first maternal attribute and a second physiological trait indicative of a second maternal attribute, defining, using the processing circuitry, the maternal attribute using at least the first maternal physiological trait and the second maternal physiological trait.

Example 68: The method of any of examples 61-67, further comprising: generating, using the processing circuitry, a plurality of maternal attributes as the processing circuitry receives the output signal, and comparing, using the processing circuitry, the plurality of maternal attributes to the maternal limit.

Example 69: The method of any of examples 61-68, further comprising: sensing, using the one or more sensor, a first physiological characteristic indicative of a first fetal attribute and a second physiological characteristic indicative of a second fetal attribute, and defining, using the processing circuitry, the fetal attribute using at least the first fetal physiological attribute and the second fetal physiological attribute.

Example 70: The method of any of examples 61-69, further comprising: generating, using the processing circuitry, a plurality of fetal attributes as the processing circuitry receives the output signal, and comparing, using the processing circuitry, the plurality of fetal attributes to the fetal limit.

Example 71: The method of any of examples 61-70, further comprising communicating, using the processing circuitry, the communication to device circuitry of at least one of a patient input/output device, an external device, or a clinician IO device to cause at least one of a patient input/output device, an external device, or a clinician IO device to provide an output sensible by the maternal patient, a clinician, or another user when the processing circuitry issues the communication.

Example 72: The method of any of examples 61-71, further comprising communicating, using the processing circuitry, data indicative of at least one the maternal physiological trait, a patient physiological parameter indicative of the maternal physiological trait, the maternal attribute, the fetal physiological trait, a fetal physiological parameter indicative of the fetal physiological trait, or the fetal attribute to device circuitry of at least one of a patient input/output device, an external device, or a clinician IO device.

Example 73: The method of any of examples 61-72, further comprising: generating, using the processing circuitry, a plurality of maternal attributes as the processing circuitry receives the output signal, and defining, using the processing circuitry, the maternal limit using the plurality of maternal attributes.

Example 74: The method of any of examples 61-73, further comprising: generating, using the processing circuitry, a plurality of fetal attributes as the processing circuitry receives the output signal, and defining, using the processing circuitry, the fetal limit using the plurality of fetal attributes.

Example 75: The method of any of examples 61-74, further comprising selecting, using the processing circuitry, one or more treatment recommendations based on the communication.

Example 76: The method of example 75, further comprising communicating, using the processing circuitry, the treatment recommendations to device circuitry mechanically supported by a patient input/output device to cause the patient input/output device to provide an output sensible by the maternal patient, a clinician, or another user indicative of the treatment recommendations.

Example 77: The method of any of examples 61-76, further comprising: comparing, using the processing circuitry, the maternal attribute and an individual maternal limit comprising the maternal limit, and issuing, using the processing circuitry, the communication based on the comparison of the maternal attribute and the individual maternal limit.

Example 78: The method of example 77, further comprising communicating, using the processing circuitry, a tier I patient communication when the maternal attribute is outside of a first maternal limit, a tier II patient communication when the maternal attribute is outside of a second maternal limit, and a tier III patient communication when the maternal attribute is outside of a third maternal limit.

Example 79: The method of any of examples 61-78, further comprising: comparing, using the processing circuitry, the fetal attribute and an individual fetal limit comprising the fetal limit, and issuing, using the processing circuitry, the communication based on the comparison of the fetal attribute and the individual fetal limit.

Example 80: The method of example 79, further comprising communicating, using the processing circuitry, a tier I patient communication when the fetal attribute is outside of a first fetal limit, a tier II fetal communication when the fetal attribute is outside of a second fetal limit, and a tier III fetal communication when the fetal attribute is outside of a third fetal limit.

Example 81: The method of any of examples 61-80, further comprising at least one of: comparing, using the processing circuitry, the maternal attribute to the maternal limit using a machine learning algorithm, or comparing, using the processing circuitry, the fetal attribute to the fetal limit using the machine learning algorithm.

Example 82: The method of example 81, further comprising: receiving, by the processing circuitry, an input from a clinician input/output device, wherein the input is indicative of an assessed risk to the maternal patient when the processing circuitry issued a previously issued communication and a previously defined maternal attribute, and training, using the processing circuitry, the machine learning algorithm using a training data set indicative of the previously defined maternal attribute and the indicative input.

Example 83: The method of example 82, further comprising, using the processing circuitry, updating the training set of the machine learning algorithm based on the maternal attribute.

Example 84: The method of example 82 or example 83, further comprising updating, using the processing circuitry, the training set of the machine learning algorithm based on the indicative input.

Example 85: The method of example 81, further comprising: receiving, by the processing circuitry the input from the clinician input/output device, wherein the input is indicative of an assessed risk to the fetal patient when the processing circuitry issued a previously issued communication and a previously defined fetal attribute, and training, using the processing circuitry, the machine learning algorithm using a training data set indicative of the previously defined fetal attribute and the indicative input.

Example 86: The method of example 85, further comprising updating, using the processing circuitry, the training set of the machine learning algorithm based on the fetal attribute.

Example 87: The method of example 85 or example 86, further comprising updating, using the processing circuitry, the training set of the machine learning algorithm based on the indicative input.

Example 88: The method of any of examples 61-87, further comprising:

receiving, using the processing circuitry, an input from a clinician input/output device, wherein the input is indicative of an assessed risk to the maternal patient when the processing circuitry issued a previously issued communication and a previously defined maternal attribute, and defining, using the processing circuitry, the maternal limit using a machine learning algorithm, wherein the machine learning algorithm is trained using a training data set indicative of the previously defined maternal attribute and the indicative communication.

Example 89: The system any of examples 61-88, further comprising: receiving, by the processing circuitry, an input from a clinician input/output device, wherein the input is indicative of an assessed risk to the fetal patient when the processing circuitry issued a previously issued communication and a previously defined fetal attribute, and defining, using the processing circuitry, the fetal limit using a machine learning algorithm, wherein the machine learning algorithm is trained using a training data set indicative of the previously defined fetal attribute and the indicative communication.

Example 90: The method of any of examples 61-89, further comprising defining, using the processing circuitry, the maternal limit using a machine learning algorithm, wherein the machine learning algorithm is trained using maternal attributes sensed from a population of other patients carrying a fetal patient.

Example 91: The method of any of examples 61-90, further comprising defining, using the processing circuitry, the fetal limit using a machine learning algorithm, wherein the machine learning algorithm is trained using fetal attributes sensed from a population of other fetal patients carried by other patients.

Example 92: The method of examples 61-91, further comprising: comparing, using the processing circuitry, the maternal attribute to the maternal limit, wherein the maternal limit describes a threshold for a specific condition of the maternal patient, or comparing, using the processing circuitry, the fetal attribute to the patient fetal limit, wherein the fetal limit describes a threshold for a specific condition of the fetal patient.

Example 93: The method of example 92, wherein at least one of: the maternal attribute is indicative of a heartrate of the maternal patient and the specific condition of the maternal patient is one of a maximum heartrate of the maternal patient or a minimum heart rate of the maternal patient, or the fetal attribute is indicative of a heartrate of the fetal patient and the specific condition of the fetal patient is one of a maximum heartrate of the fetal patient or a minimum heart rate of the fetal patient.

Example 94: The method of example 92 or example 93, wherein at least one of: the maternal attribute is indicative of a systolic blood pressure of the maternal patient and the specific condition of the maternal patient is one of a maximum systolic blood pressure of the maternal patient or a minimum systolic blood pressure of the maternal patient, or the fetal attribute is indicative of a systolic blood pressure of the fetal patient and the specific condition of the fetal patient is one of a maximum systolic blood pressure of the fetal patient or a minimum systolic blood pressure of the fetal patient.

Example 95: The method of any of examples 92-94, wherein at least one of: the maternal attribute is indicative of a diastolic blood pressure of the maternal patient and the specific condition of the maternal patient is one of a maximum diastolic blood pressure of the maternal patient or a minimum diastolic blood pressure of the maternal patient, or the fetal attribute is indicative of a diastolic blood pressure of the fetal patient and the specific condition of the fetal patient is one of a maximum diastolic blood pressure of the fetal patient or a minimum diastolic blood pressure of the fetal patient.

Example 96: The method of any of examples 92-95, wherein at least one of: the maternal attribute is indicative of an oxygen saturation level of the maternal patient and the specific condition of the maternal patient is one of a maximum oxygen saturation level of the maternal patient or a minimum oxygen saturation level of the maternal patient, or the fetal attribute is indicative of an oxygen saturation level of the fetal patient and the specific condition of the fetal patient is one of a maximum oxygen saturation level of the fetal patient or a minimum oxygen saturation level of the fetal patient.

Example 97: The method of any of examples 92-96, wherein at least one of: the maternal attribute is indicative of a respiration rate of the maternal patient and the specific condition of the maternal patient is one of a maximum respiration rate of the maternal patient or a minimum respiration rate of the maternal patient, or the fetal attribute is indicative of a respiration rate of the fetal patient and the specific condition of the fetal patient is one of a maximum respiration rate of the fetal patient or a minimum respiration rate of the fetal patient.

Example 98: The method of any of examples 92-97, wherein at least one of: the maternal attribute is indicative of a temperature of the maternal patient and the specific condition of the maternal patient is one of a maximum temperature of the maternal patient or a minimum temperature of the maternal patient, or the fetal attribute is indicative of a temperature of the fetal patient and the specific condition of the fetal patient is one of a maximum temperature of the fetal patient or a minimum temperature of the fetal patient.

Example 99: The method of any of examples 92-98, wherein at least one of: the maternal attribute is indicative of an activity level of the maternal patient and the specific condition of the maternal patient is one of a maximum activity level of the maternal patient or a minimum activity level of the maternal patient, or the fetal attribute is indicative of an activity level of the fetal patient and the specific condition of the fetal patient is one of a maximum activity level of the fetal patient or a minimum activity level of the fetal patient.

Example 100: The method of any of examples 92-99, wherein the maternal attribute is indicative of a muscular contraction of the maternal patient, and wherein the specific condition of the maternal patient is one of false labor or maternal labor.

Example 101: The method of any of examples 92-100, wherein the maternal attribute is indicative of a blood glucose level of the maternal patient and the specific condition of the maternal patient is one of a maximum blood glucose level of the maternal patient or a minimum blood glucose level of the maternal patient.

Example 102: The method of any of examples 92-101, wherein the maternal attribute is indicative of a weight of the maternal patient, and wherein the specific condition of the maternal patient is one of a maximum weight of the maternal patient or a minimum weight of the maternal patient.

Example 103: The system of any of examples 92-102, wherein the maternal attribute is indicative of a level of amniotic fluid of the maternal patient, and wherein the specific condition of the maternal patient is one of minimum amniotic fluid level of the maternal patient or a maximum amniotic fluid level of the maternal patient.

Example 104: The method of any of examples 61-103, wherein at least one of: the maternal physiological trait is an electrocardiogram of the maternal patient, or the fetal physiological trait is an electrocardiogram of the fetal patient.

Example 105: The method of any of examples 61-104, wherein at least one of: the maternal physiological trait is an echocardiogram of the maternal patient, or the fetal physiological trait is an echocardiogram of the fetal patient.

Example 106: The method of any of examples 61-105, wherein at least one of: the maternal physiological trait is an audible sound generated by the maternal patient, or the fetal physiological trait is an audible sound generated by the fetal patient.

Example 107: The method of any of examples 61-106, wherein at least one of: the maternal physiological trait is an accelerometer signal indicative of a movement of the maternal patient, or the fetal physiological trait is an accelerometer signal indicative of a movement of the fetal patient.

Example 108: The method of any of examples 61-107, wherein at least one of: the maternal physiological trait is an electromyography signal indicative of a muscle contraction of the maternal patient, or the fetal physiological trait is an electromyography signal indicative of a muscle contraction of the fetal patient.

Example 109: The method of any of examples 61-108, wherein at least one of: the maternal physiological trait is an oxygen saturation signal indicative of an oxygen saturation of the maternal patient, or the fetal physiological trait is an oxygen saturation signal indicative of an oxygen saturation of the fetal patient.

Example 110: The method of any of examples 61-109, wherein at least one of: the maternal physiological trait is an optical signal influenced by the body of the maternal patient, or the fetal physiological trait is an optical signal influenced by the body of the fetal patient.

Example 111. A system comprising processing circuitry configured to perform the method of any one or more of examples 61-110.

Example 112. A non-transitory computer readable storage medium comprising program instructions configured to cause processing circuitry to perform the method of any one or more of examples 61-111.

Example 113. A system comprising: one or more sensors configured in an implantable medical device to sense at least one of a maternal physiological trait indicative of a maternal attribute of a maternal patient or a fetal physiological trait indicative of a fetal attribute of a fetal patient carried by the maternal patient, wherein the maternal attribute is indicative of a physiological characteristic of a body of the maternal patient and the fetal attribute is indicative of a physiological characteristic of a body of the fetal patient; sensing circuitry operably coupled to the one or more sensors and configured to issue an output signal indicative of at least one of the maternal physiological trait or the fetal physiological trait; and processing circuitry operably connected to the sensing circuitry, wherein the processing circuitry is configured to: receive the output signal from the sensing circuitry, generate an output based at least in part on at least one of the maternal attribute or the fetal attribute for the received output signal.

Example 114: The system of example 113, wherein the implantable medical device comprises an insertable cardiac monitor, the insertable cardiac monitor comprising a distal electrode, a proximal electrode, and circuitry comprising a processer within the housing, the circuitry configured to sense the at least one of the maternal physiological trait indicative of the maternal attribute of the maternal patient or the fetal physiological trait indicative of the fetal attribute of the fetal patient carried by the maternal patient.

Example 115: The system of example 113 comprising any of the foregoing system examples, wherein the one or more sensors are configured in the implantable medical device to sense at least one of a maternal physiological trait indicative of a maternal attribute of a maternal patient or a fetal physiological trait indicative of a fetal attribute of a fetal patient carried by the maternal patient, and wherein the implantable medical device comprises an insertable cardiac monitor further comprising a distal electrode, a proximal electrode, and circuitry comprising a processer within the housing, the circuitry configured to sense the at least one of the maternal physiological trait indicative of the maternal attribute of the maternal patient or the fetal physiological trait indicative of the fetal attribute of the fetal patient carried by the maternal patient.

Various examples have been described. These and other examples are within the scope of the following claims.

What is claimed is:

1. A system comprising:

one or more sensors configured to sense a maternal physiological trait indicative of a maternal attribute of a maternal patient, a first fetal physiological trait indicative of a fetal attribute of a fetal patient carried by the maternal patient, and a second fetal physiological trait indicative of the fetal attribute of the fetal patient, wherein the maternal attribute is indicative of a physiological characteristic of a body of the maternal patient and the fetal attribute is indicative of a physiological characteristic of a body of the fetal patient;

sensing circuitry operably coupled to the one or more sensors and configured to issue a first electrical output signal indicative of the maternal physiological trait, a second electrical output signal indicative of the first fetal physiological trait, and a third electrical output signal indicative of the second fetal physiological trait; and processing circuitry operably connected to the sensing circuitry, wherein the processing circuitry is configured to:

receive the first electrical output signal, the second electrical output signal, and the third electrical output signal from the sensing circuitry, define the maternal attribute for the received first electrical output signal, define the fetal attribute based on the second electrical output signal and the third electrical output signal, and issue a communication based on at least one of:

a comparison of the maternal attribute and a maternal limit, wherein the maternal limit defines a threshold for the maternal attribute, or a comparison of the fetal attribute and a fetal limit, wherein the fetal limit defines a threshold for the fetal attribute.

2. The system of claim 1, wherein:

the one or more sensors are configured to sense a mixed physiological trait indicative of a second maternal physiological trait and a third fetal physiological trait, the output signal comprises a combined electrical signal that is indicative of the mixed physiological trait, and the processing circuitry is configured to:

separate the combined electrical signal into an electrical output signal indicative of the second maternal physiological trait and an electrical output signal indicative of the third fetal physiological trait, and define a second maternal attribute for the electrical output signal indicative of the second maternal physiological trait and define a second fetal attribute for the electrical output signal indicative of the third fetal physiological trait.

3. The system of claim 1, wherein:

the maternal attribute is at least one of a heartrate of the maternal patient, a systolic blood pressure of the maternal patient, a diastolic blood pressure of the maternal patient, an oxygen saturation level of the maternal patient, a respiration rate of the maternal patient, a temperature of the maternal patient, a muscular contraction of the maternal patient, a blood glucose level of the maternal patient, or a weight of the maternal patient.

4. The system of claim 1, wherein:

the fetal attribute is at least one of a heartrate of the fetal patient, a systolic blood pressure of the fetal patient, a diastolic blood pressure of the fetal patient, an oxygen saturation level of the fetal patient, a respiration rate of the fetal patient, an activity of a fetal patient, or a temperature of the fetal patient.

5. The system of 1, wherein:

the processing circuitry is configured to receive a designated start of a pregnancy of the maternal patient as an input from a user input device, the processing circuitry is configured to determine an elapsed time since the designated start of the pregnancy, and the processing circuitry is configured to select the maternal limit and the fetal limit based the elapsed time.

6. The system of claim 1, wherein the one or more sensors are configured to sense a first physiological trait indicative of a first maternal attribute and a second physiological trait indicative of a second maternal attribute, and wherein the maternal attribute is based on at least the first physiological trait and the second physiological trait.

7. The system of claim 1, wherein the processing circuitry is configured to issue the communication to device circuitry of a patient input/output device to cause the patient input/output device to provide an output sensible by the maternal patient, a clinician, or another user when the processing circuitry issues the communication.

8. The system of claim 1, wherein the processing circuitry is configured to communicate physiological data indicative of at least one of the maternal physiological trait, the maternal attribute, the fetal physiological trait, or the fetal attribute to device circuitry of at least one of a patient input/output device, a clinician input/output device, or an external device communicatively coupled to the clinician input/output device.

9. The system of claim 1, wherein the processing circuitry is configured to at least one of:

generate a plurality of maternal attributes as the processing circuitry receives the output signal, and wherein the processing circuitry is configured to define the maternal limit using the plurality of maternal attributes; or generate a plurality of fetal attributes as the processing circuitry receives the output signal, and wherein the processing circuitry is configured to define the fetal limit using the plurality of fetal attributes.

10. The system of claim 1, further comprising a medical device configured to contact a body of the maternal patient, wherein the medical device mechanically supports the sensor and at least some portion of the sensing circuitry.

11. The system of claim 1, wherein the processing circuitry is configured to select treatment recommendations based on the communication, and wherein the processing circuitry is configured to communicate the treatment recommendations to device circuitry mechanically supported by a patient input/output device to cause the patient input/output device to provide an output sensible by the maternal patient, a clinician, or another user indicative of the treatment recommendations.

12. The system of claim 1, wherein to issue the communication, the processing circuitry is further configured to:

compare, using a machine learning algorithm, at least one of: the maternal attribute to the maternal limit or the fetal attribute to the fetal limit.

13. The system of claim 1, wherein the processing circuitry is configured to issue the communication to a device located at a different physical location than the one or more sensors.

14. The system of claim 1, further comprising communication circuitry, wherein the processing circuitry is configured to issue the communication via the communication circuitry.

* * * * *